(12) United States Patent
Hsieh et al.

(10) Patent No.: US 8,710,079 B2
(45) Date of Patent: Apr. 29, 2014

(54) QUINOLINE COMPOUNDS AND THEIR USE FOR TREATING VIRAL INFECTION

(75) Inventors: Hsing-Pang Hsieh, Zhunan (TW); Tsu-An Hsu, Taipei (TW); Jiann-Yih Yeh, Zhunan (TW); Yu-Sheng Chao, New York, NY (US)

(73) Assignee: National Health Research Institutes, Zhunan Town (TW)

( * ) Notice: Subject to any disclaimer, the term of this patent is extended or adjusted under 35 U.S.C. 154(b) by 146 days.

(21) Appl. No.: 13/091,895

(22) Filed: Apr. 21, 2011

(65) Prior Publication Data

US 2011/0263620 A1  Oct. 27, 2011

Related U.S. Application Data

(60) Provisional application No. 61/327,390, filed on Apr. 23, 2010.

(51) Int. Cl.
*C07D 215/38* (2006.01)
*A61K 31/04* (2006.01)

(52) U.S. Cl.
USPC .......................... 514/312; 546/159

(58) Field of Classification Search
USPC .......................... 546/159; 514/312
See application file for complete search history.

(56) References Cited

U.S. PATENT DOCUMENTS

| 5,523,408 A * | 6/1996 | Batt et al. ............... 546/167 |
| 5,578,609 A * | 11/1996 | Batt et al. ............... 514/314 |
| 2008/0015193 A1 | 1/2008 | Mendoza et al. |

FOREIGN PATENT DOCUMENTS

WO   WO 01/24785 A2   4/2001

OTHER PUBLICATIONS

Batt, Bloorg & MEd Chem Lett, vol. 8, pp. 1745-1750, 1998.*
Buu-Hoi, CA 42:23261, abstract only of Recueil desTravaux Chimiques des Pays-Bas et de la Belgique, vol. 66, pp. 533-543, 1947.*
Zong, J Org Chen, vol. 73, pp. 4334-4337, 2008.*
Saudi, Arch Pharm Pharm Med Chem, vol. 336, pp. 165-174, 2003.*
Pokhodylo, Russian J Gen Chem, vol. 79, No. 2, pp. 309-314, 2009.*
Buu-Hoi, J Org Chem, 1953, vol. 18, pp. 1209-1224.*
Horak et al., *Ukranica Bioorganica Acta* 1 (2008) 49-54.

* cited by examiner

*Primary Examiner* — D M Seaman
(74) *Attorney, Agent, or Firm* — Knobbe Martens Olson & Bear LLP

(57) ABSTRACT

Quinoline compounds of formula (I):

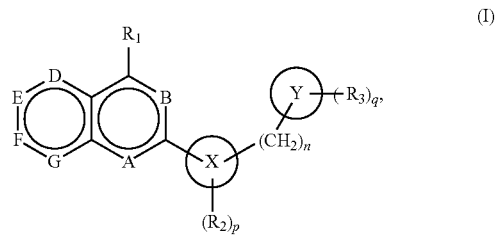

in which A, B, D, E, F, G, $R_1$, $R_2$, $R_3$, X, Y, n, p, and q are defined herein. Also disclosed is a method for treating a viral infection with a compound of formula (I).

12 Claims, No Drawings

QUINOLINE COMPOUNDS AND THEIR USE FOR TREATING VIRAL INFECTION

RELATED APPLICATIONS

This application claims priority under 35 U.S.C. §119(e) to U.S. Provisional Application No. 61/327,390, filed Apr. 23, 2010, the entire contents of which are incorporated herein by reference.

BACKGROUND

There are a wide variety of viruses that cause various disorders, ranging from common human ailments (e.g., common cold, flu, chickenpox, and cold sore) to serious human diseases (e.g., Ebola, avian influenza, AIDS, and SARS). Some viruses are established causes of malignancy in humans and other animals. For example, papillomavirus, hepatitis B and hepatitis C virus, Epstein-Barr virus, and human T-lymphotropic virus have been associated with human cancers.

One of the most effective treatments of viral diseases is use of antiviral drugs. Different antiviral drugs target different stages of the viral life cycle. Taking influenza treatment for example, conventional anti-influenza drugs inhibit the membrane fusion or replication step by targeting viral hemagglutinin, neuraminidase, M2 ion channel, or 3P polymerase complex, or host factors such as kinases, as described in, e.g., Hsieh et al., *Current Pharmaceutical Design*, 2007, 13, 3531-3542.

Quinoline compounds, a binding ligand of nucleic acid, have been studied for their therapeutic use.

SUMMARY OF THE INVENTION

This invention is based on the discovery that certain quinoline compounds have potent anti-virus activity. Thus, this invention relates to quinoline compounds and to their uses in the treatment of an infection with a virus, especially influenza virus.

In one aspect, this invention features a quinoline compound of formula (I):

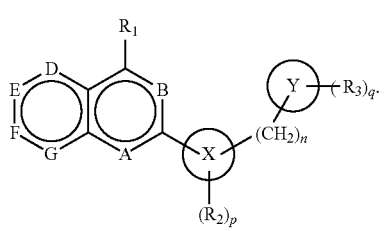

In this formula, each of A, B, D, E, F, and G, independently, is N or CR and at least one of them is N, R being H, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, cyano, amino, hydroxy, alkoxy, aryloxy, $C(O)R_a$, $C(O)OR_a$, $C(O)NR_aR_b$, $C(S)R_a$, $C(NR_a)R_b$, $NR_aR_b$, or $NR_a$CONR$_b$R$_c$, in which each of $R_a$, $R_b$, and $R_c$, independently, is H, alkyl, alkenyl, alkynyl, hydroxy, alkoxy, aryloxy, amino, cycloalkyl, cycloalkenyl, heterocycloalkyl, heterocycloalkenyl, aryl, or heteroaryl; $R_1$ is alkoxy, $C(O)R_d$, $C(O)OR_d$, $CONR_dR_e$, $SO_2R_d$, or CN, in which each of $R_d$ and $R_e$, independently, is H, alkyl, alkenyl, alkynyl, hydroxy, alkoxy, aryloxy, amino, cycloalkyl, cycloalkenyl, heterocycloalkyl, heterocycloalkenyl, aryl, or heteroaryl; each of $R_2$ and $R_3$, independently, is optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, cyano, amino, hydroxy, alkoxy, aryloxy, $C(O)R_f$, $C(O)OR_f$, $C(O)NR_fR_g$, $C(S)R_f$, $C(NR_f)R_g$, $NR_fR_g$, or $NR_f$CONR$_g$R$_h$, in which each of $R_f$, $R_g$, and $R_h$, independently, is H, alkyl, alkenyl, alkynyl, hydroxy, alkoxy, aryloxy, amino, cycloalkyl, cycloalkenyl, heterocycloalkyl, heterocycloalkenyl, aryl, or heteroaryl; each of X and Y, independently, is arylene or heteroarylene having 1-4 heteroatoms independently selected from the group consisting of N, S, and O; n is 0, 1, 2, 3, 4, or 5; p is 1, 2, 3, or 4; and q is 0, 1, 2, 3, 4, 5, 6, or 7, provided that the compound of formula (I) is not any one of compounds 3.1-3.42 disclosed in Ukrainica Bioorganica Acta 1 (2008) 49-54 incorporated herein by reference and is not any one of compounds I3K5, I3K55, I3K46, I3K52, I3K53, I1K52, I1K46, I1K53, I1K55, I2K5, I3K4, I3K36, I2K46, I2K55, I2K51, I2K52, I3K51, I3K6, I3K44, I2K42, I2K43, I3K42, I2K20, I3K43, or I1K44, or Brequinar disclosed in WO01/24785 incorporated herein by reference. In some embodiments, X is a heteroarylene containing at least one N atom. In some embodiments, Y is arylene or a heteroarylene having 1-4 heteroatoms independently selected from the group consisting of N, S, and O.

A subset of the just-described compounds are those in which X is 5-membered heteroarylene containing at least one N atom, e.g.,

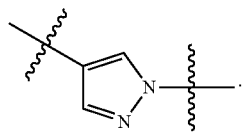

In these compounds, A can be N; each of B, D, E, F, and G can be CR; n can be 0; Y can be phenyl; $R_1$ can be $C(O)OR_d$, or $R_2$ can be alkyl.

The Compounds described above include the compounds themselves, as well as their salts, their solvates, and their prodrugs, if applicable. A salt, for example, can be formed between an anion and a positively charged group (e.g., amino) on a quinoline compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on a quinoline compound. Suitable cations include sodium ion, potassium ion, magnesium ion, calcium ion, and an ammonium cation such as tetramethylammonium ion. The quinoline compounds also include those salts containing quaternary nitrogen atoms. Examples of prodrugs include esters and other pharmaceutically acceptable derivatives, which, upon administration to a subject, are capable of providing active quinoline compounds.

In another aspect, this invention features a method for treating an infection with a virus by administering to a subject in need thereof an effective amount of a quinoline compound described above. In some embodiments of this aspect of the invention, the compounds 3.1-3.42 disclosed in Ukrainica Bioorganica Acta 1 (2008) 49-54 and compounds I3K5, I3K55, I3K46, I3K52, I3K53, I1K52, I1K46, I1K53, I1K55, I2K5, I3K4, I3K36, I2K46, I2K55, I2K51, I2K52, I3K51, I3K6, I3K44, I2K42, I2K43, I3K42, I2K20, I3K43, or I1K44, or Brequinar disclosed in WO01/24785 are not excluded. Examples of the infections to be treated include, but are not limited to, influenza virus, human rhinovirus 2, Herpes simplex virus, enterovirus 71 (EV 71), Coxsackie Virus B3, Hepatitis C virus, Hepatitis B virus, Epstein-Barr virus (EBV), and Human Immunodeficiency Virus.

In another aspect, this invention provides a pharmaceutical composition comprising a pharmaceutically acceptable carrier and a compound as described above.

Also within the scope of this invention is the therapeutic use of the above-described quinoline compounds and use of the compounds for the manufacture of a medicament for treating a disorder such as an infection with a virus.

2-(5-methyl-1-phenyl-1H-pyrazol-4-yl)quinoline-4-carboxylic acid and its analogs, as well as their therapeutic use as described above, are also contemplated.

The details of one or more embodiments of the invention are set forth in the description below. Other features, objects, and advantages of the invention will be apparent from the description and the claims.

DETAILED DESCRIPTION OF THE PREFERRED EMBODIMENT

The term "alkyl" refers to a straight or branched monovalent hydrocarbon containing, unless otherwise stated, 1-20 carbon atoms (e.g., $C_1$-$C_{10}$). Examples of alkyl include, but are not limited to, methyl, ethyl, n-propyl, i-propyl, n-butyl, i-butyl, and t-butyl. The term "alkenyl" refers to a straight or branched monovalent or bivalent hydrocarbon containing 2-20 carbon atoms (e.g., $C_2$-$C_{10}$) and one or more double bonds. Examples of alkenyl include, but are not limited to, ethenyl, propenyl, propenylene, allyl, and 1,4-butadienyl. The term "alkynyl" refers to a straight or branched monovalent or bivalent hydrocarbon containing 2-20 carbon atoms (e.g., $C_2$-$C_{10}$) and one or more triple bonds. Examples of alkynyl include, but are not limited to, ethynyl, ethynylene, 1-propynyl, 1- and 2-butynyl, and 1-methyl-2-butynyl. The term "alkoxy" refers to an —O-alkyl radical. Examples of alkoxy include, but are not limited to, methoxy, ethoxy, n-propoxy, isopropoxy, n-butoxy, iso-butoxy, sec-butoxy, and tert-butoxy. The term "acyloxy" refers to an —O—C(O)—R radical in which R can be H, alkyl, alkenyl, alkynyl, cycloalkyl, cycloalkenyl, heterocycloalkyl, heterocycloalkenyl, aryl, or heteroaryl. The term "amino" refers to NH$_2$, alkylamino, or arylamino. The term "alkylamino" refers to an —N(R)-alkyl radical in which R can be H, alkyl, alkenyl, alkynyl, cycloalkyl, cycloalkenyl, heterocycloalkyl, heterocycloalkenyl, aryl, or heteroaryl. The terms "amido" and "carbamido" refer to —NRC(O)R' and —C(O)NRR' radicals respectively, in which each of R and R', independently, can be H, alkyl, alkenyl, alkynyl, cycloalkyl, cycloalkenyl, heterocycloalkyl, heterocycloalkenyl, aryl, or heteroaryl.

The term "cycloalkyl" refers to a monovalent or bivalent saturated hydrocarbon ring system having 3 to 30 carbon atoms (e.g., $C_3$-$C_{12}$). Examples of cycloalkyl include, but are not limited to, cyclopropyl, cyclobutyl, cyclopentyl, cyclohexyl, 1,4-cyclohexylene, cycloheptyl, cyclooctyl, and adamantine. The term "cycloalkenyl" refers to a monovalent or bivalent non-aromatic hydrocarbon ring system having 3 to 30 carbons (e.g., $C_3$-$C_{12}$) and one or more double bonds. Examples include cyclopentenyl, cyclohexenyl, and cycloheptenyl. The term "heterocycloalkyl" refers to a monovalent or bivalent nonaromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, dioxanyl, morpholinyl, and tetrahydrofuranyl. The term "heterocycloalkenyl" refers to a monovalent or bivalent nonaromatic 5-8 membered monocyclic, 8-12 membered bicyclic, or 11-14 membered tricyclic ring system having one or more heteroatoms (such as O, N, S, or Se) and one or more double bonds.

The term "aryl" refers to a monovalent 6-carbon monocyclic, 10-carbon bicyclic, 14-carbon tricyclic aromatic ring system. Examples of aryl groups include, but are not limited to, phenyl, naphthyl, and anthracenyl. The term "arylene" refers to a bivalent 6-carbon monocyclic, 10-carbon bicyclic, 14-carbon tricyclic aromatic ring system. The term "aryloxyl" refers to an —O-aryl. The term "arylamino" refers to an —N(R)-aryl in which R can be H, alkyl, alkenyl, alkynyl, cycloalkyl, cycloalkenyl, heterocycloalkyl, heterocycloalkenyl, aryl, or heteroaryl. The term "heteroaryl" refers to a monvalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, and thiazolyl. The term "heteroarylene" refers to a bivalent aromatic 5-8 membered monocyclic, 8-12 membered bicyclic, or 11-14 membered tricyclic ring system having one or more heteroatoms (such as O, N, S, or Se).

Optionally substituted alkyl, optionally substituted alkenyl, optionally substituted alkynyl, optionally substituted cycloalkyl, optionally substituted heterocycloalkyl, optionally substituted cycloalkenyl, optionally substituted heterocycloalkenyl, optionally substituted amino, optionally substituted aryl, and optionally substituted heteroaryl mentioned above include both substituted and unsubstituted moieties. Possible substituents on amino, cycloalkyl, heterocycloalkyl, cycloalkenyl, heterocycloalkenyl, aryl, arylene, heteroaryl, and heteroarylene include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl (—C(O)NH$_2$), carboxyl (—COOH), and carboxylic ester. On the other hand, possible substituents on alkyl, alkenyl, alkynyl, or alkylene include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

In one aspect, this invention features a quinoline compound of formula (I):

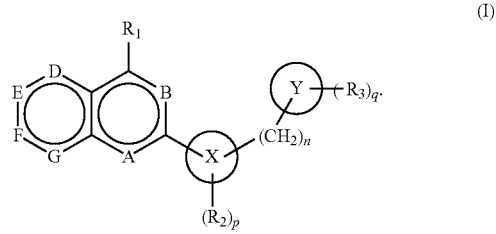

In this formula, each of A, B, D, E, F, and G, independently, is N or CR and at least one of them is N, R being H, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, cyano, amino, hydroxy, alkoxy, aryloxy, C(O)R$_a$, C(O)OR$_a$, C(O)NR$_a$R$_b$, C(S)R$_a$, C(NR$_a$)R$_b$, NR$_a$R$_b$, or NR$_a$CONR$_b$R$_c$, in which each of R$_a$, R$_b$, and R$_c$, independently, is H, alkyl, alkenyl, alkynyl, hydroxy, alkoxy, aryloxy, amino, cycloalkyl, cycloalkenyl, heterocycloalkyl, heterocycloalkenyl, aryl, or heteroaryl; R$_1$ is alkoxy, C(O)R$_d$, C(O)OR$_d$, CONR$_d$R$_e$, SO$_2$R$_d$, or CN, in which each of R$_d$ and R$_e$, independently, is H, alkyl, alkenyl, alkynyl, hydroxy, alkoxy, aryloxy, amino, cycloalkyl, cycloalkenyl, heterocycloalkyl, heterocycloalkenyl, aryl, or heteroaryl; each of R$_2$ and R$_3$, independently, is optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, cyano, amino, hydroxy, alkoxy, aryloxy, C(O)R$_f$, C(O)OR$_f$, C(O)NR$_f$R$_g$, C(S)R$_f$, C(NR$_f$)R$_g$, NR$_f$R$_g$, or NR$_f$CONR$_g$R$_h$, in which each of R$_f$, R$_g$, and R$_h$, independently, is H, alkyl, alkenyl, alkynyl, hydroxy, alkoxy, aryloxy, amino, cycloalkyl, cycloalkenyl, heterocycloalkyl, heterocycloalkenyl, aryl, or heteroaryl; each of X and Y, independently, is arylene or heteroarylene having 1-4 heteroatoms independently selected from the group consisting of N, S, and O; n is 0, 1, 2, 3, 4, or 5; p is 1, 2, 3, or 4; and q is 0, 1, 2, 3, 4, 5, 6, or 7, provided that the compound of formula (I) is not any one of compounds 3.1-3.42 disclosed in Ukrainica Bioorganica Acta 1 (2008) 49-54 incorporated herein by reference and is not any one of compounds I3K5, I3K55, I3K46, I3K52, I3K53, I1K52, I1K46, I1K53, I1K55, I2K5, I3K4, I3K36, I2K46, I2K55, I2K51, I2K52, I3K51, I3K6, I3K44, I2K42, I2K43, I3K42, I2K20, I3K43, or I1K44, or Brequinar disclosed in WO01/24785 incorporated herein by reference. In some embodiments, X is a heteroarylene containing at least one N atom. In some embodiments, Y is arylene or a heteroarylene having 1-4 heteroatoms independently selected from the group consisting of N, S, and O.

In some embodiments, X is heteroarylene containing at least one N atom. In some embodiments, X is 5-membered heteroarylene containing at least one N atom, e.g.,

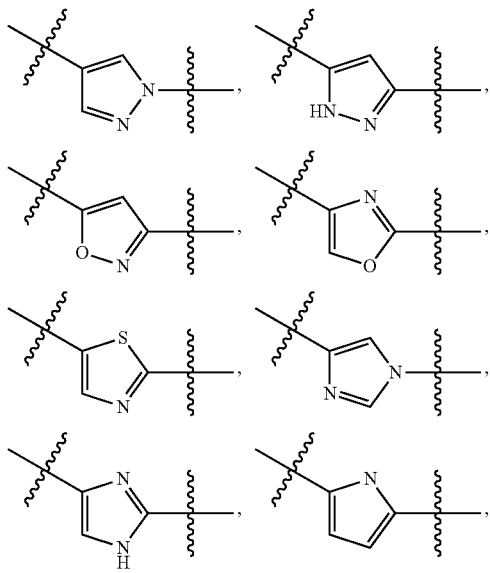

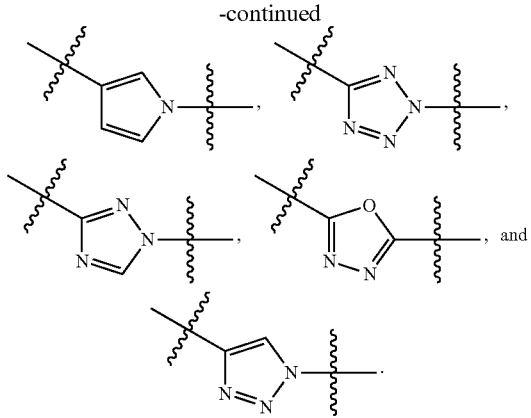

A subset of the just-described compounds are those in which X is

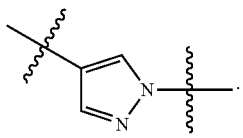 [SMILES: *c1cnn(*)c1]

In other embodiments, X is 5-membered heteroarylene containing at least one O atom. In these compounds, A can be N; each of B, D, E, F, and G can be CR; n can be 0; Y can be phenyl; R$_1$ can be C(O)OR$_d$, or R$_2$ can be H or alkyl.

In some embodiments, only one of X and Y can be phenyl or thienyl. In some embodiments, at least one of X and Y is phenyl. In some embodiments, X is a heteroarylene containing at least one N atom, and Y is arylene or a heteroarylene having 1-4 heteroatoms independently selected from the group consisting of N, S, and O.

In some embodiments, A can be N; each of B, D, E, F, and G can be CR; R is selected from the group consisting of H, alkyl optionally substituted with halo, optionally substituted aryl, halo; R$_1$ is C(O)OR$_d$, in which R$_d$ is H or alkyl; each of R$_2$ and R$_3$, independently, is alkyl optionally substituted with hydroxyl or halo, C(O)OR$_f$, halo, nitro, hydroxy, alkoxy, or phenyl, wherein R$_f$ is H or alkyl; each of X and Y, independently, is arylene or heteroarylene having 1-4 heteroatoms independently selected from the group consisting of N, S, and O; n is 0, or 5; p is 1 or 2; and q is 0, 1, 2, or 3. In some embodiments, X is a heteroarylene containing at least one N atom, and Y is arylene or a heteroarylene having 1-4 heteroatoms independently selected from the group consisting of N, S, and O.

The compounds described above include the compounds themselves, as well as their salts, their solvates, and their prodrugs, if applicable. A salt, for example, can be formed between an anion and a positively charged group (e.g., amino) on a quinoline compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on a quinoline compound. Suitable cations include sodium ion, potassium ion, magnesium ion, calcium ion, and an ammonium cation such as tetramethylammonium ion. The quinoline compounds also include those salts containing quaternary nitrogen atoms. Examples of prodrugs include esters and other pharmaceutically acceptable derivatives, which, upon administration to a subject, are capable of providing active quinoline compounds.

In another aspect, this invention features a method for treating an infection with a virus by administering to a subject in need thereof an effective amount of a quinoline compound described above. Examples of the virus include, but are not limited to, influenza virus, human rhinovirus 2, Herpes simplex virus, enterovirus 71 (EV 71), Coxsackie Virus B3, Hepatitis C virus, Hepatitis B virus, Epstein-Barr virus (EBV), and Human Immunodeficiency Virus. In another aspect, a pharmaceutical composition comprising a pharmaceutically acceptable carrier and a compound as described above is also provided.

Also within the scope of this invention is the therapeutic use of the above-described quinoline compounds and use of the compounds for the manufacture of a medicament for treating a disorder such as an infection with a virus.

2-(5-methyl-1-phenyl-1H-pyrazol-4-yl)quinoline-4-carboxylic acid and its analogs, as well as their therapeutic use as described above, are also contemplated.

Shown below are exemplary compounds of this invention:

compound 1

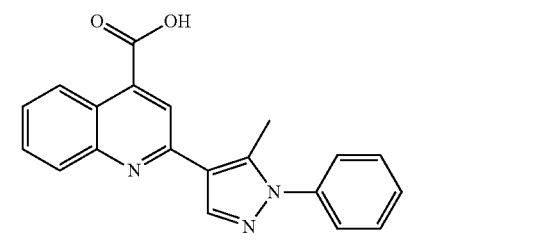

compound 2

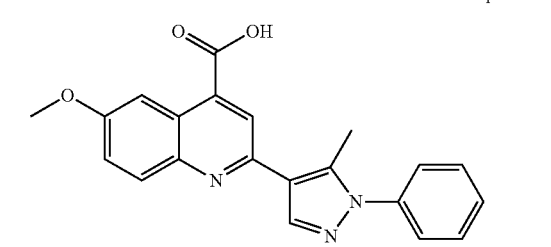

compound 3

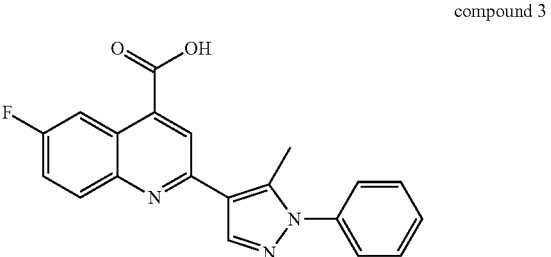

compound 4

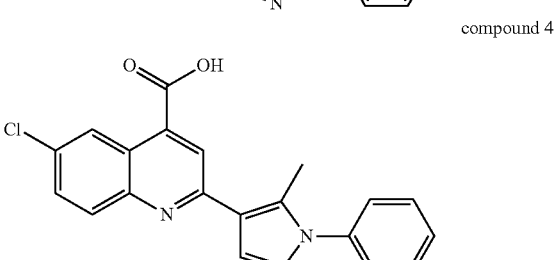

compound 5

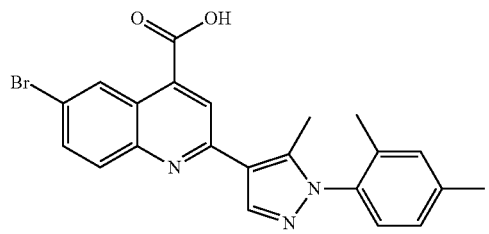

compound 6

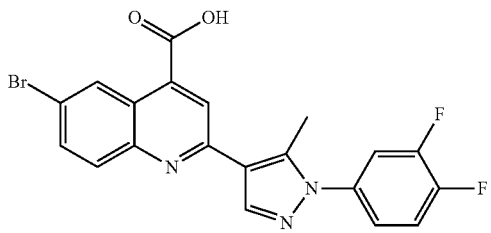

compound 7

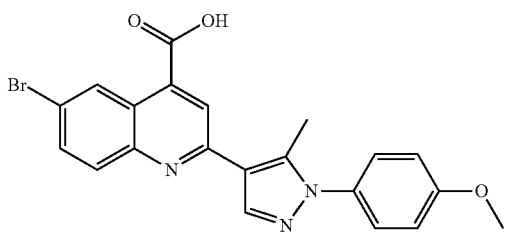

compound 8

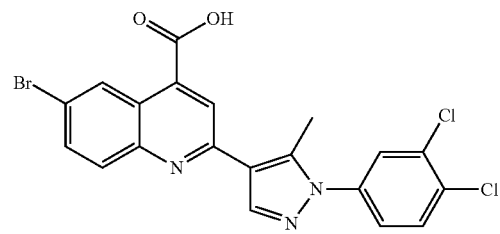

compound 9

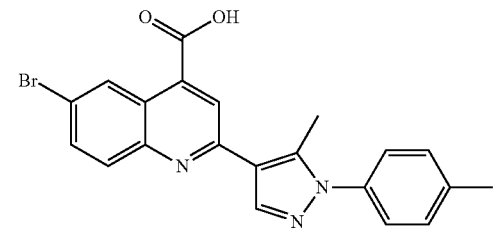

compound 10

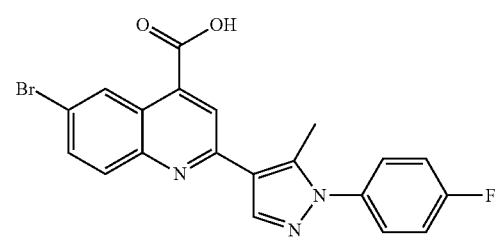

-continued
compound 11
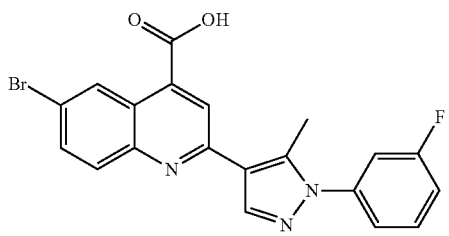
compound 12
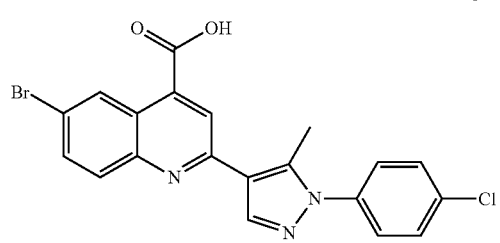
compound 13
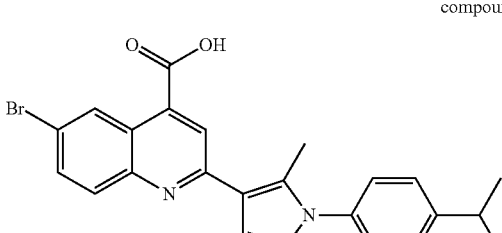
compound 14
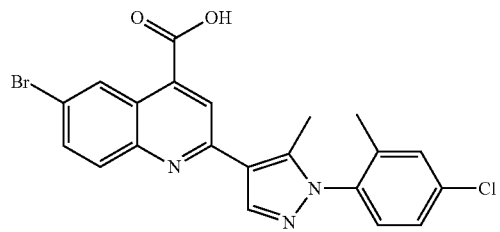
compound 15
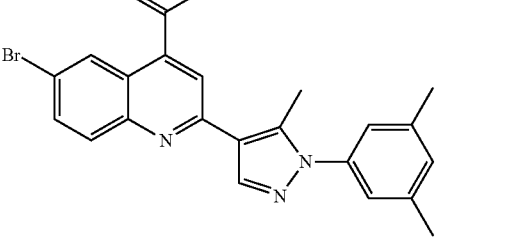
Compound 16
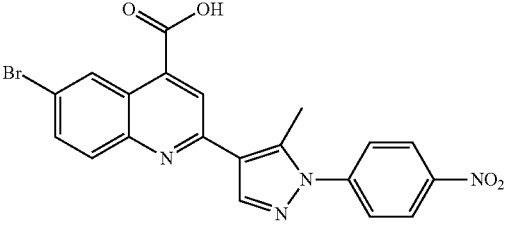
Compound 17
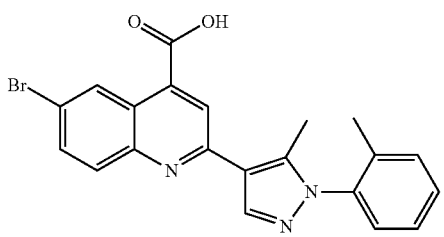
Compound 18
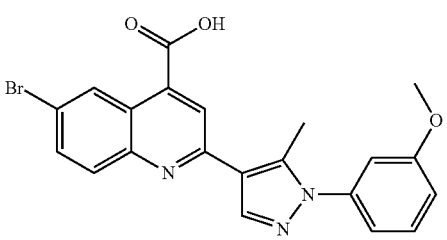
Compound 19
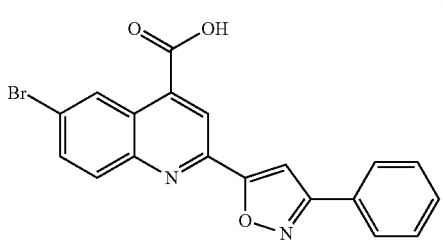
Compound 20
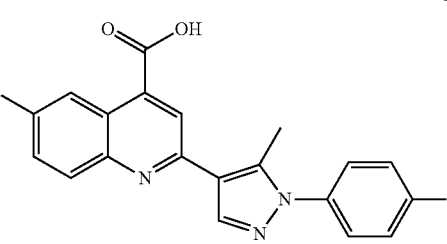
Compound 21
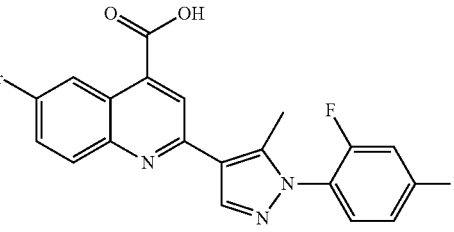
Compound 22
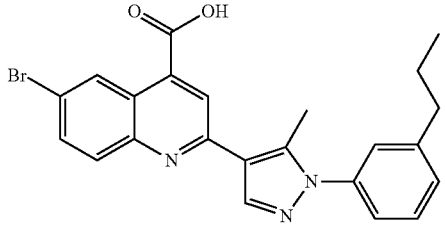

Compound 23
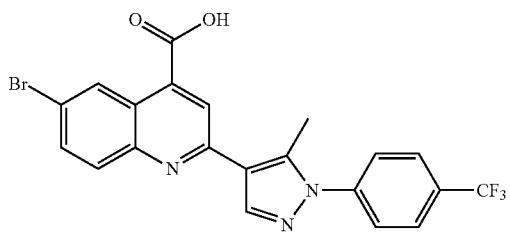
Compound 24
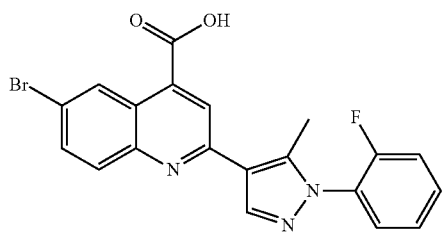
Compound 25
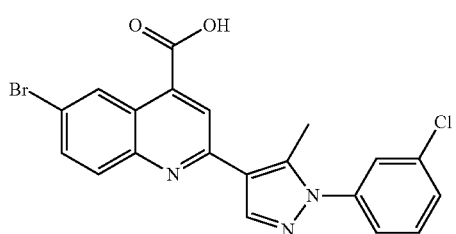
Compound 26
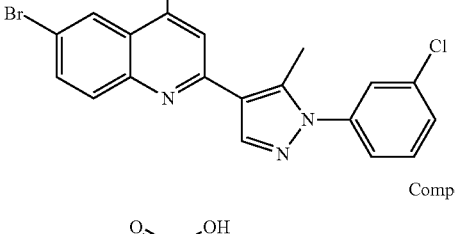
Compound 27
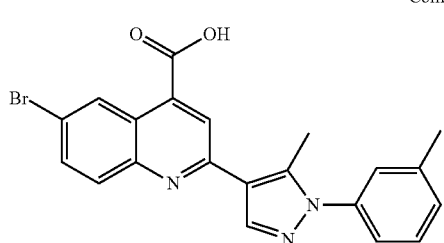
Compound 28
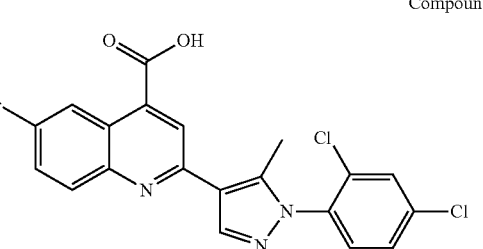
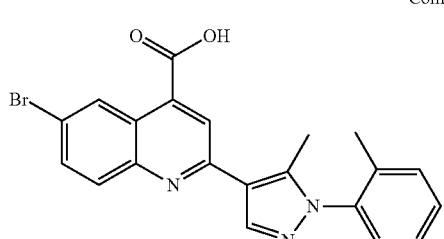
Compound 29
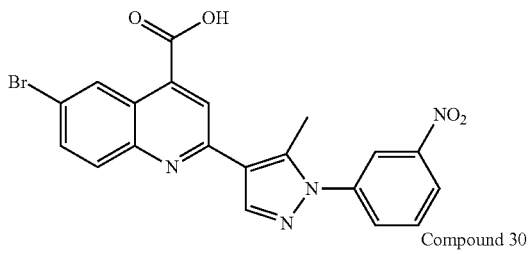
Compound 30
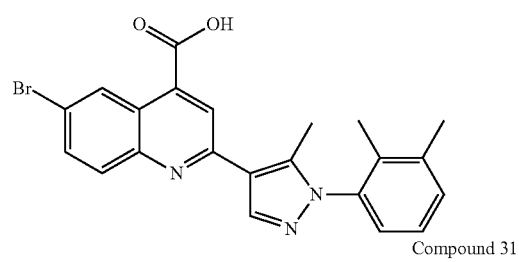
Compound 31
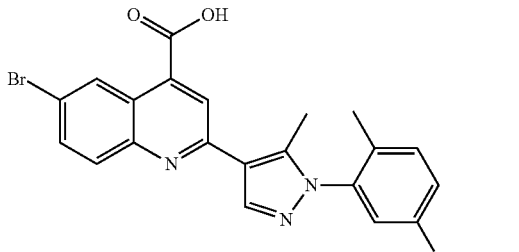
Compound 32
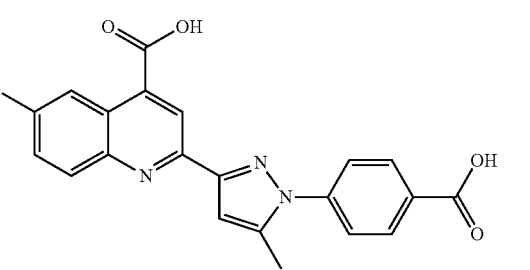
Compound 33
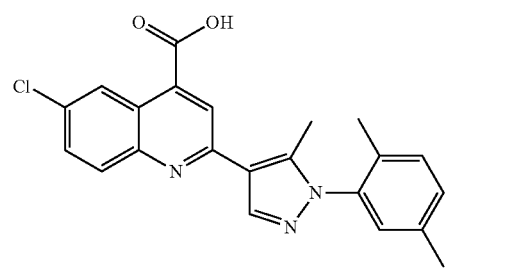
Compound 34
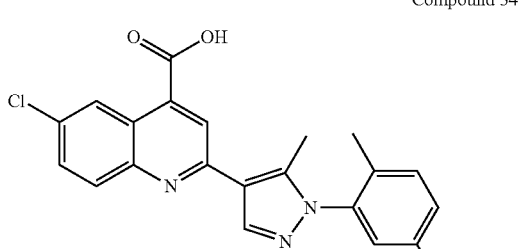

Compound 35
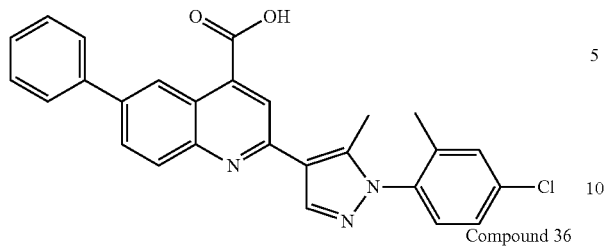
Compound 36
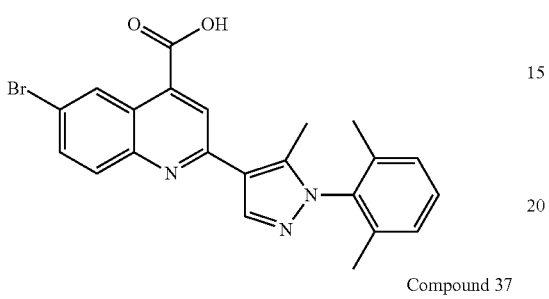
Compound 37
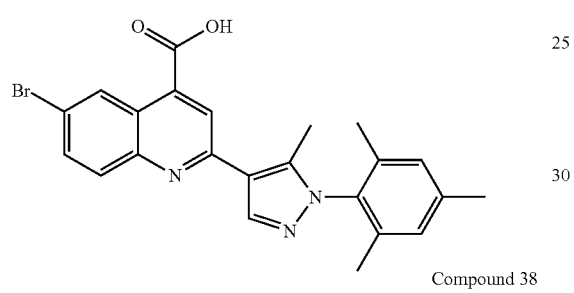
Compound 38
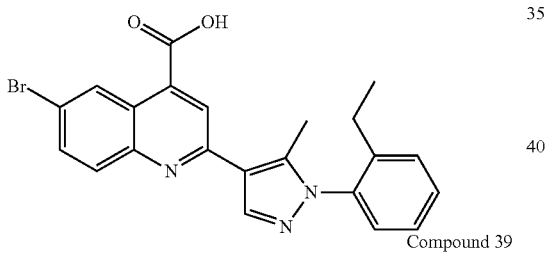
Compound 39
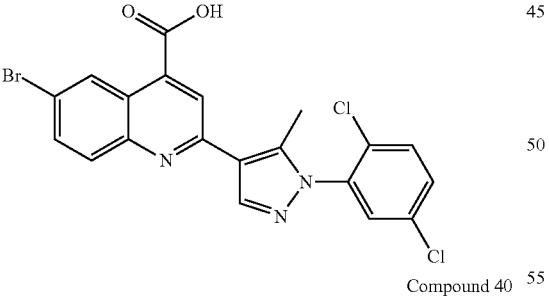
Compound 40
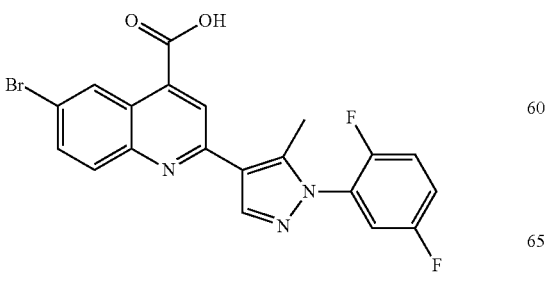
Compound 41
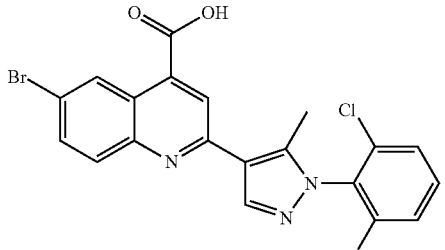
Compound 42
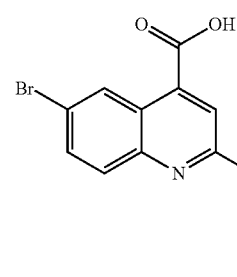
Compound 43
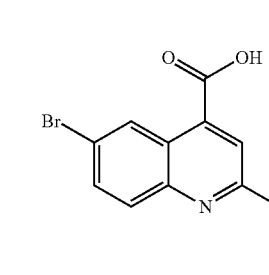
Compound 44
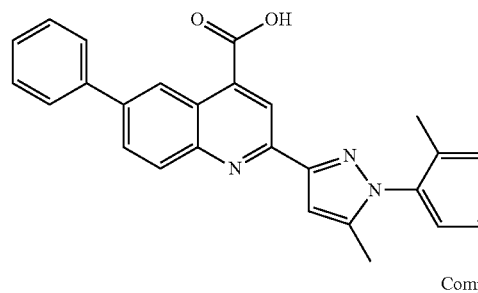
Compound 45
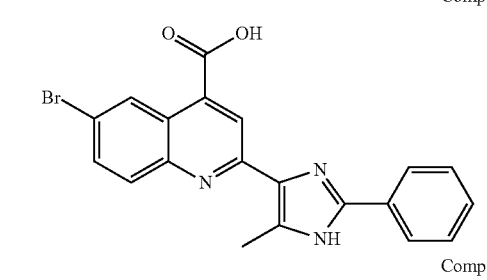
Compound 46
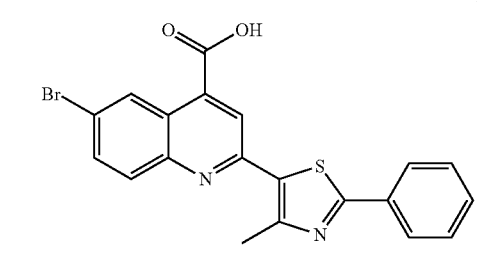

Compound 47
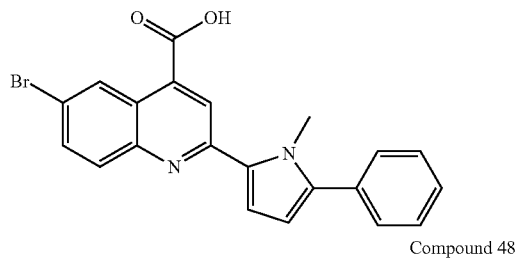
Compound 48
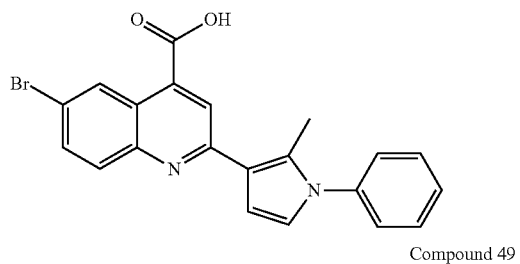
Compound 49
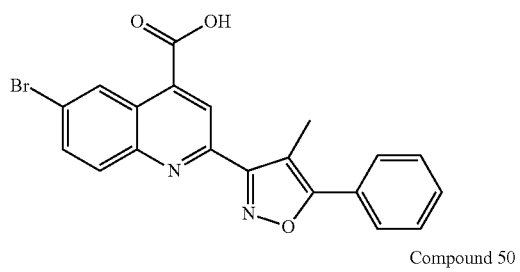
Compound 50
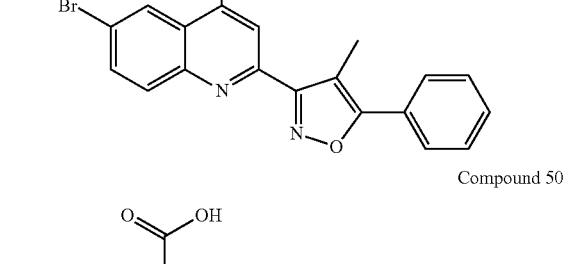
Compound 51
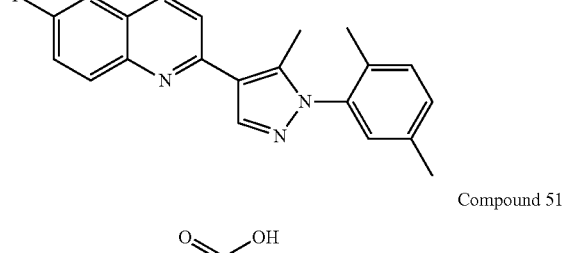
Compound 52
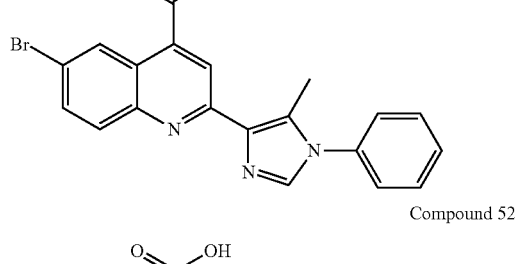
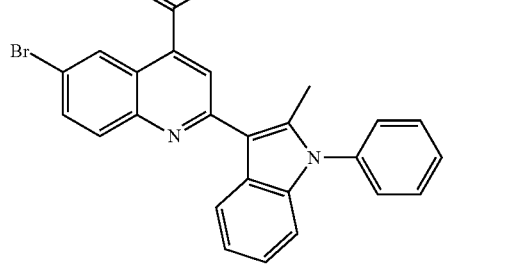
Compound 53
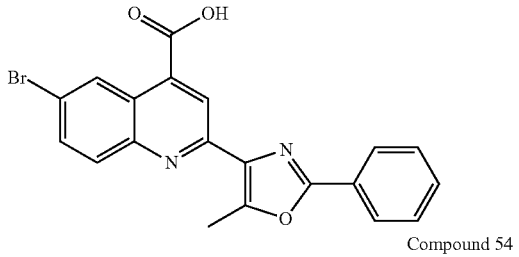
Compound 54
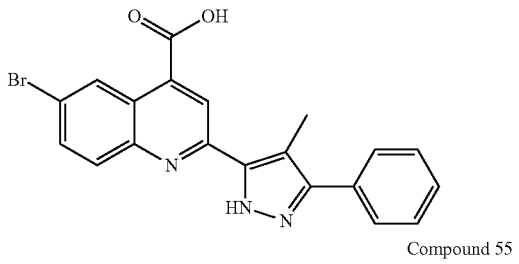
Compound 55
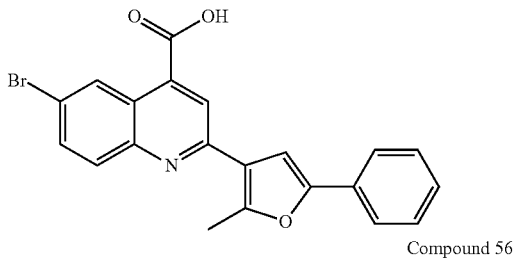
Compound 56
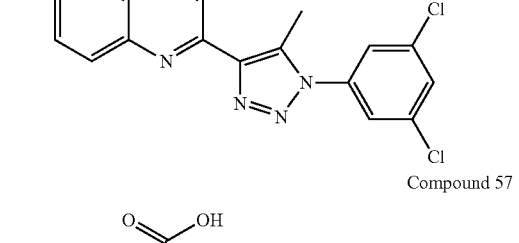
Compound 57
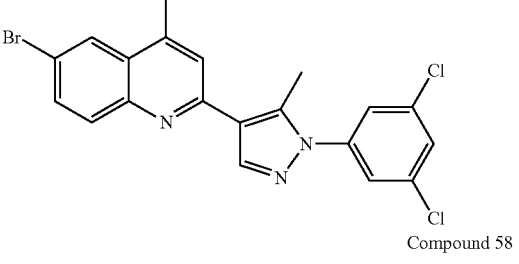
Compound 58
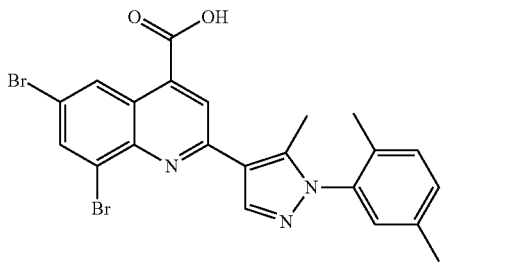

-continued
Compound 59
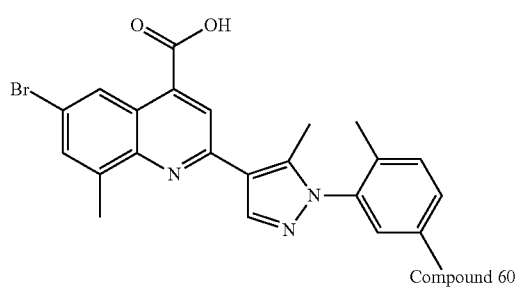
Compound 60
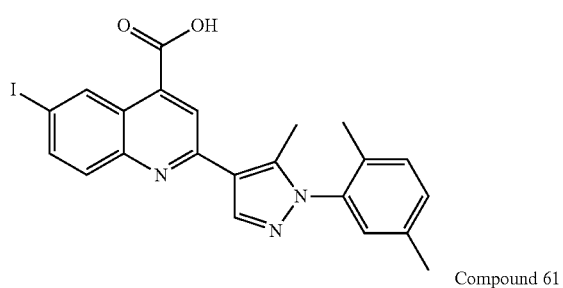
Compound 61
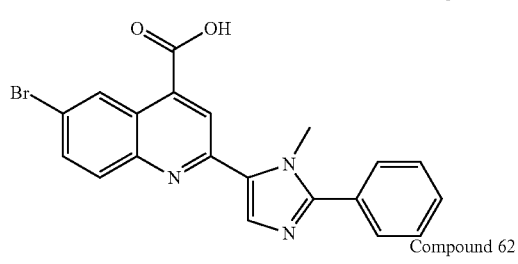
Compound 62
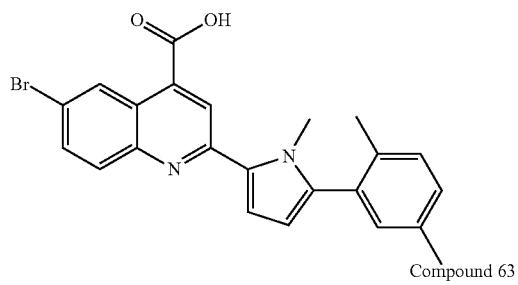
Compound 63
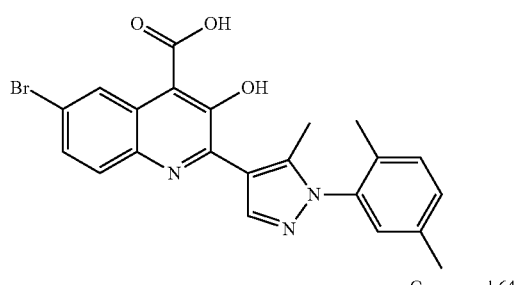
Compound 64
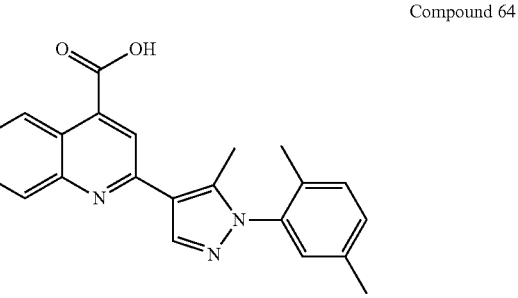
-continued
Compound 65
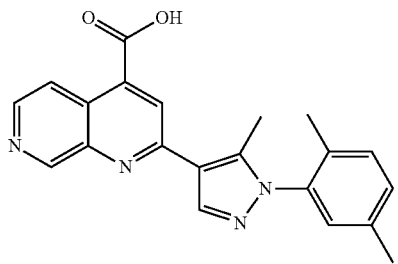
Compound 66
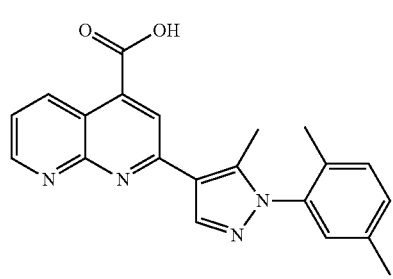
Compound 67
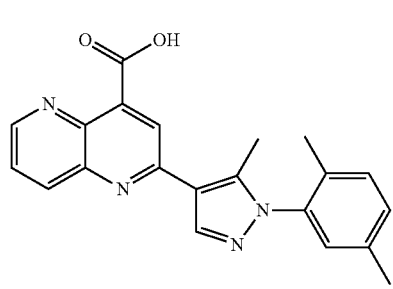
Compound 68
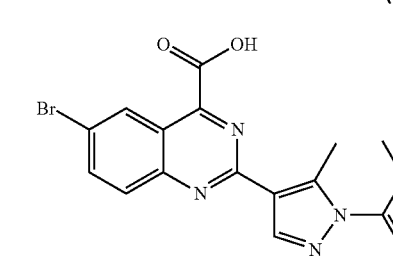
Compound 69
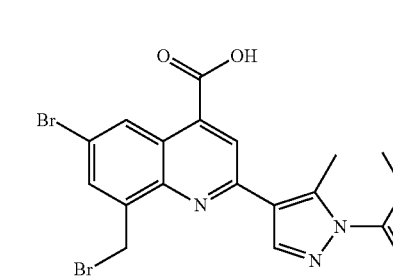
Compound 70
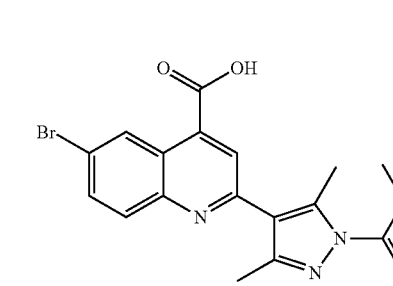

Compound 71
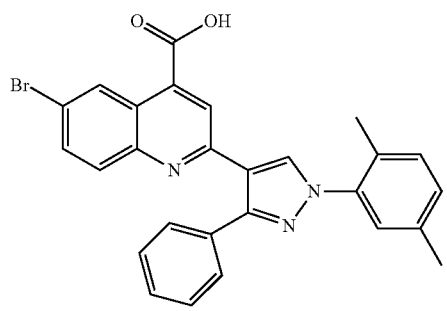
Compound 72
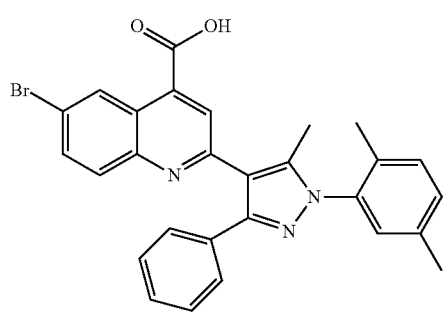
Compound 73
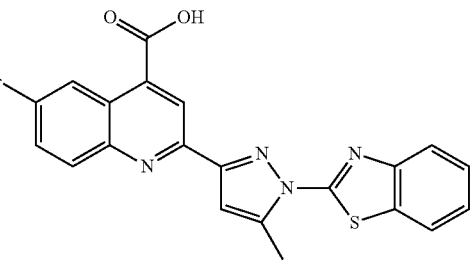
Compound 74
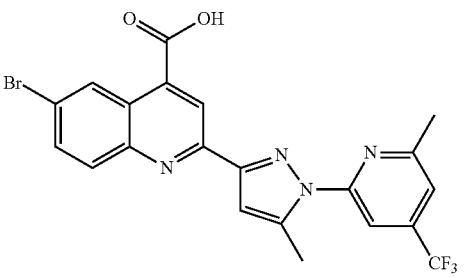
Compound 75
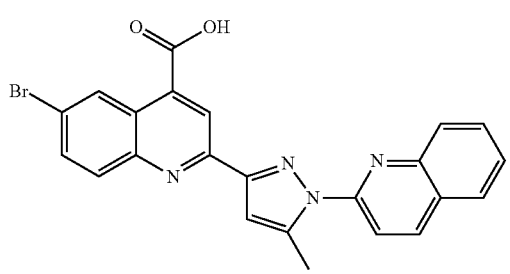
Compound 76
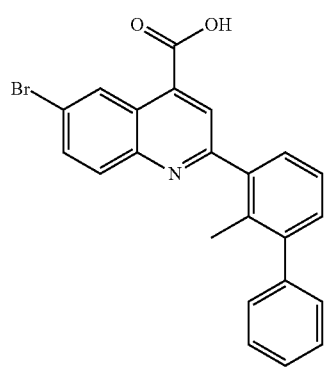
77
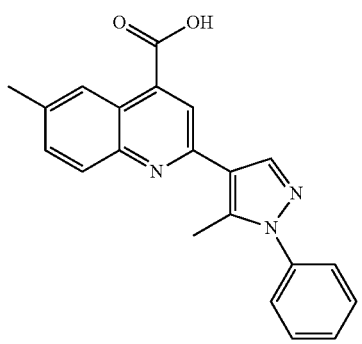
78
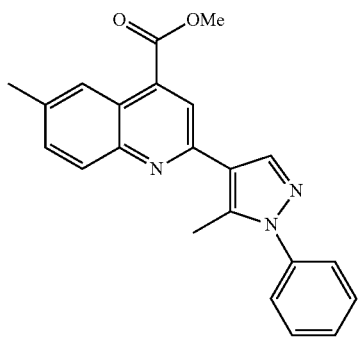
79
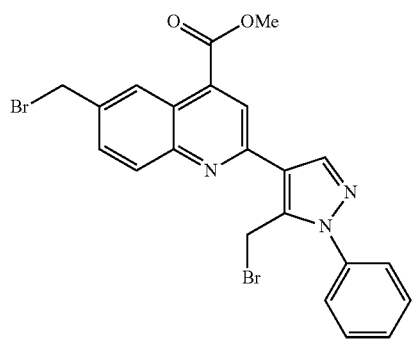

80
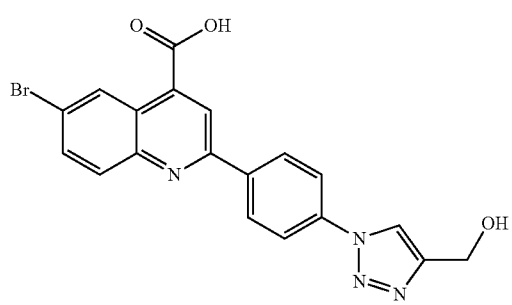
81
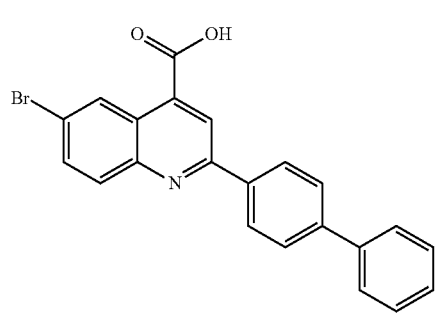
82
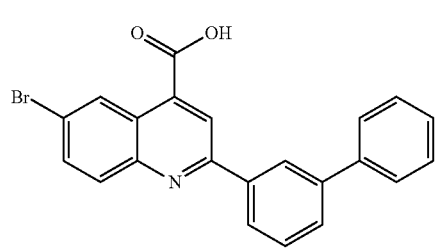
83
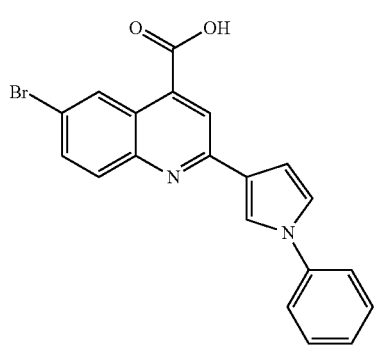
84
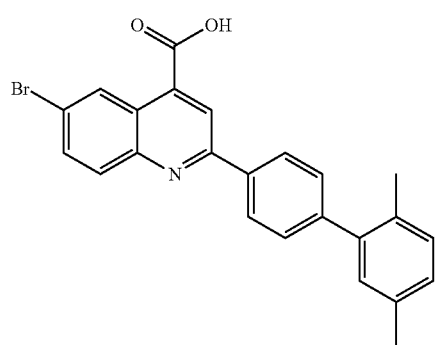
85
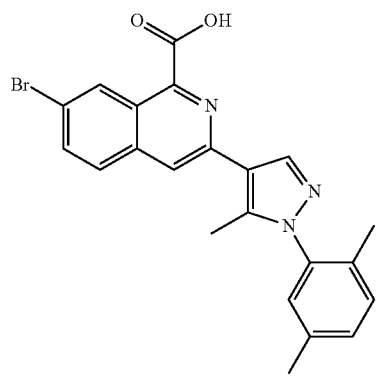
86
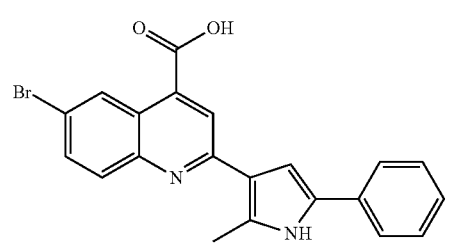
87
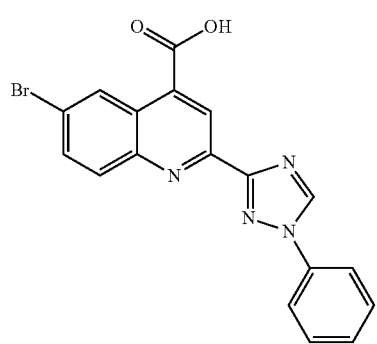
88
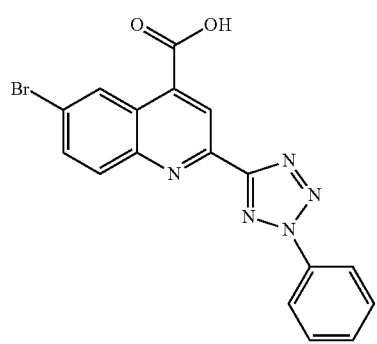
89
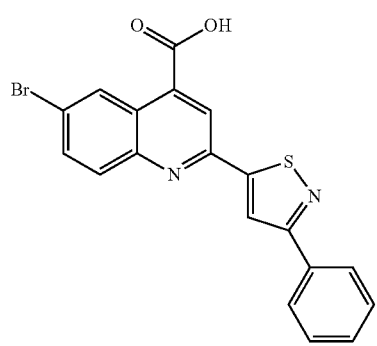

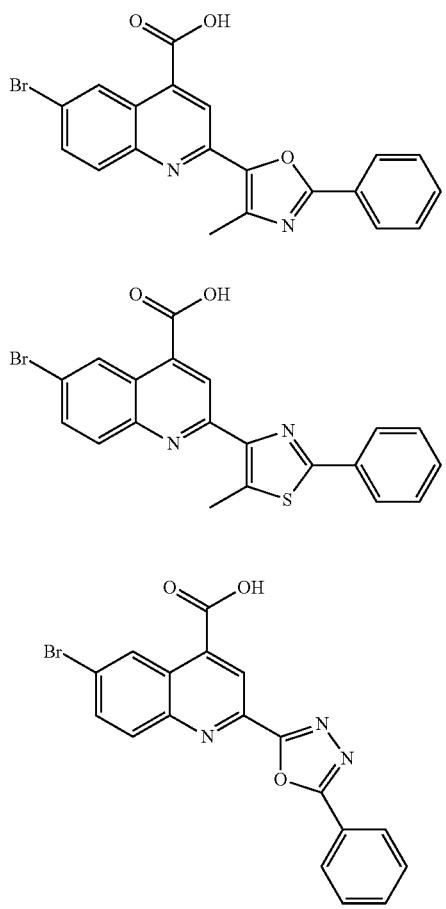

Scheme 1

A quinoline compound thus synthesized can be further purified by flash column chromatography, high performance liquid chromatography, crystallization, or any other suitable methods.

The quinoline compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

The viral infection that can be treated by the method of the invention includes infections caused by various viruses such as DNA viruses (e.g., Adenoviridae, Herpesviridae, Poxyiridae, and Parvoviridae); RNA viruses (e.g., Enteroviruses, SARS, influenza, and hepatitis C); and reverse transcribing viruses (e.g., Human immunodeficiency virus).

The quinoline compounds described herein can be administered in conjunction with another therapeutic agent for treating a viral infection such as influenza and AIDS. Examples of the other therapeutic agents include but are not limited to protease inhibitors (e.g., nafamostat, camostat, gabexate, epsilon-aminocapronic acid and aprotinin), fusion inhibitors (e.g., BMY-27709, CL 61917, and CL 62554), M2 proton channel blockers (e.g., Amantadine and Rimantadine), polymerase inhibitors (e.g., 2-deoxy-2'fluoroguanosides (2'-fluoroGuo), 6-fluoro-3-hydroxy-2-pyrazinecarboxamide (T-705), T-705-4-ribofuranosyl-5'-triphosphate (T-705RTP)), endonuclease inhibitors (e.g., L-735,822 and flutimide), kinase inhibitors (e.g., U0126 (a MEK inhibitor), PD098059 (a MEK-specific inhibitor), PD-184352/CI-1040 (a MEK inhibitor), PD 0325901 (a MEK inhibitor), ARRY-142886/AZD-6244 (a MEK1 and MEK2 inhibitor)), neuraminidase inhibitors (e.g., Zanamivir (Relenza), Oseltamivir (Tamiflu), Peramivir and ABT-675 (A-315675)), all of which were described in Hsieh et al., *Current Pharmaceutical Design*, 2007, 13, 3531-3542. Other examples of antiviral drugs that can be administered in conjunction with the quinoline compounds described herein include, but are not limited to, reverse transcriptase inhibitor (e.g., Abacavir, Adefovir, Delavirdine, Didanosine, Efavirenz, Emtricitabine, Lamivudine, Nevirapine, Stavudine, Tenofovir, Tenofovir disoproxil, and Zalcitabine) Aciclovir, Acyclovir, protease inhibitor (e.g., Amprenavir, Indinavir, Nelfinavir, Ritonavir, and Saquinavir), Arbidol, Atazanavir, Atripla, Boceprevir, Cidofovir, Combivir, Darunavir, Docosanol, Edoxudine, entry inhibitors (e.g., Enfuvirtide and Maraviroc), Entecavir, Famciclovir, Fomivirsen, Fosamprenavir, Foscarnet, Fosfonet, Ganciclovir, Ibacitabine, Immunovir, Idoxuridine, Imiqui- The quinoline compounds described herein can be prepared by conventional chemical transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof. The quinoline compounds can also be synthesized in manners similar to those described in: (a) Giuseppe et al., *J. Med. Chem.* 1997, 40, 1794-1807. (b) Kaila et al., *J. Med. Chem.* 2007, 50, 40-64. (c) Kaila et al., *J. Med. Chem.* 2007, 50, 21-39. (d) Xiang et al., *Bioorg. Med. Chem. Lett.* 2001, 11, 541-544, with necessary modifications as recognized by those skilled in the art.

The route shown in Scheme 1 exemplifies synthesis of the quinoline compounds of the present invention. Isatins (i) (e.g., 1.0 mmol), appropriate ketone (ii) (e.g., 1.0 mmol), and KOH (e.g., 5.0 mmol) in H₂O (e.g., 3 mL) is refluxed for 8 h. The reaction mixture is washed twice with Et₂O (e.g., 30 mL). The ice-cold aqueous phase is acidified to pH 1 with 1 N HCl(aq), and the precipitate is collected by suction filtration, washed with H₂O, and dried to give quinoline (iii).

mod, Inosine, integrase inhibitor (e.g., Raltegravir), interferons (e.g., types I, II, and III), Lopinavir, Loviride, Moroxydine, Nexavir, nucleoside analogues (e.g., Aciclovir), Penciclovir, Pleconaril, Podophyllotoxin, Ribavirin, Tipranavir, Trifluridine, Trizivir, Tromantadine, Truvada, Valaciclovir (Valtrex), Valganciclovir, Vicriviroc, Vidarabine, Viramidine, and Zidovudine.

To practice the method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. A quinoline compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. One or more solubilizing agents (e.g., cyclodextrins) which form more soluble complexes with the quinoline compounds can be utilized as pharmaceutical carriers for delivery of the active compounds. Examples of other carriers include colloidal silicon dioxide, magnesium stearate, sodium lauryl sulfate, and D&C Yellow #10.

Suitable in vitro assays can be used to preliminarily evaluate the efficacy of the quinoline compounds in inhibiting the cytopathic effect induced by a virus. The compounds can further be examined for their efficacy in treating an infection with the virus. For example, a compound can be administered to an animal (e.g., a mouse model) having a viral infection and its therapeutic effects are then assessed. Based on the results, an appropriate dosage range and administration route can also be determined.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Synthesis of 2-(5-methyl-1-phenyl-1H-pyrazol-4-yl)-quinoline-4-carboxylic acid (Compound 1)

To a solution of isatins (1.0 mmol), 1-(5-methyl-1-phenyl-1H-pyrazol-4-yl)ethanone (1.0 mmol), and KOH (5.0 mmol) in 3 mL $H_2O$ was refluxed for 8 h. The solution was washed twice with $Et_2O$ (30 mL). The ice-cold aqueous phase was acidified to pH 1 with 1 N HCl(aq), and the precipitate was collected by suction filtration, washed with $H_2O$, and dried to give 2-(5-Methyl-1-phenyl-1H-pyrazol-4-yl)-quinoline-4-carboxylic acid (1) $^1$H NMR (300 MHz, $CDCl_3$-$d^6$-DMSO) δ 8.774 (d, J=7.8 Hz, 1H), 8.208 (d, J=8.1 Hz, 2H), 8.085 (d, J=8.1 Hz, 2H), 7.756-7.701 (m, 1H), 7.595-7.463 (m, 6H), 2.807 (s, 3H). LCMS (M+H): 330.1.

Example 2

Syntheses of Compounds 2-63 and 73-92

Compounds 2-63 and 73-92 were prepared in a manner similar to that described in Example 1. $^1$H NMR, $^{13}$C NMR and MS data of some of these compounds are listed below.

Compound 2: $^1$H NMR (300 MHz, $CDCl_3$-$d^6$-DMSO) δ 8.245-8.179 (m, 3H), 7.925 (d, J=9.6 Hz, 1H), 7.572-7.388 (m, 6H), 3.934 (s, 3H), 2.780 (s, 3H). LCMS (M+H): 360.1.

Compound 3: $^1$H NMR (300 MHz, $CDCl_3$-$d^6$-DMSO) δ 8.499 (dd, J=10.8, 3.0 Hz, 1H), 8.313 (s, 1H), 8.273 (s, 1H), 8.095 (dd, J=9.3, 3.0 Hz, 1H), 7.595-7.480 (m, 6H), 2.793 (s, 3H). LCMS (M+H): 348.0.

Compound 4: $^1$H NMR (300 MHz, $CDCl_3$-$d^6$-DMSO) δ 8.816 (d, J=2.4 Hz, 1H), 8.294 (s, 1H), 8.278 (s, 1H), 8.029 (d, J=8.7 Hz, 1H), 7.696 (dd, J=9.0, 2.4 Hz, 1H), 7.597-7.460 (m, 5H), 2.795 (s, 3H). $^{13}$C NMR (75 MHz, $CDCl_3$-$d^6$-DMSO) δ 167.039, 152.807, 146.883, 139.323, 138.795, 138.753, 135.315, 130.727, 129.869, 128.829, 127.869, 124.985, 124.336, 123.341, 121.425, 119.372, 12.488. LCMS (M+H): 364.0.

Compound 5: $^1$H NMR (300 MHz, $CDCl_3$-$d^6$-DMSO) δ 9.062 (s, 1H), 8.291 (s, 1H), 8.187 (s, 1H), 7.959 (d, J=9.0 Hz, 1H), 7.769 (d, J=9.0 Hz, 1H), 7.193-7.153 (m, 2H), 2.593 (s, 3H), 2.419 (s, 3H), 2.057 (s, 3H). $^{13}$C NMR (75 MHz, $CDCl_3$-$d^6$-DMSO) δ 167.890. 153.419, 147.605, 140.497, 140.152, 139.320, 139.081, 135.650, 135.480, 132.705, 131.574, 130.998, 128.113, 127.533, 127.301, 127.218, 124.322, 121.737, 120.534, 118.754, 114.413, 21.101, 17.063, 11.921. LCMS (M+H): 436.1.

Compound 6: $^1$H NMR (300 MHz, $CDCl_3$-$d^6$-DMSO) δ 9.068 (d, J=2.1 Hz, 1H), 8.278 (s, 1H), 8.191 (s, 1H), 7.983 (d, J=9.0 Hz, 1H), 7.803 (dd, J=9.0, 2.1 Hz, 1H), 7.615-7.598 (m, 1H), 7.491-7.339 (m, 2H), 2.763 (s, 3H). LCMS (M+H): 444.0.

Compound 7: ¹H NMR (300 MHz, CDCl₃-d⁶-DMSO) δ 9.062 (s, 1H), 8.281 (s, 1H), 8.163 (s, 1H), 7.986 (d, J=9.0 Hz, 1H), 7.794 (dd, J=9.0, 1.8 Hz, 1H), 7.415 (d, J=9.0 Hz, 1H), 7.049 (d, J=9.0 Hz, 1H), 3.867 (s, 3H), 2.889 (s, 3H). LCMS (M+H): 438.0.

Compound 8: ¹H NMR (300 MHz, CDCl₃-d⁶-DMSO) δ 9.081 (d, J=2.1 Hz, 1H), 8.277 (s, 1H), 8.200 (s, 1H), 7.982 (d, J=9.0 Hz, 1H), 7.802 (dd, J=9.0, 2.1 Hz, 1H), 7.704 (d, J=2.1 Hz, 1H), 7.643 (d, J=9.0 Hz, 1H), 7.433 (dd, J=9.0, 2.1 Hz, 1H), 2.593 (s, 3H). LCMS (M+H): 475.8.

Compound 9: ¹H NMR (300 MHz, CDCl₃-d⁶-DMSO) δ 9.042 (s, 1H), 8.279 (s, 1H), 8.170 (s, 1H), 7.980 (d, J=9.0 Hz, 1H), 7.791 (d, J=9.0 Hz, 1H), 7.708-7.630 (m, 1H), 7.396-7.327 (m, 3H), 2.772 (s, 3H), 2.401 (s, 3H). ¹³C NMR (75 MHz, CDCl₃-d⁶-DMSO) δ 167.530, 153.226, 147.560, 139.305, 139.172, 138.182, 136.614, 135.127, 132.804, 131.051, 129.666, 127.992, 125.161, 124.261, 121.977, 120.709, 119.718, 21.048, 12.721. LCMS (M+H): 422.0.

Compound 10: ¹H NMR (300 MHz, CDCl₃-CD₃OD) δ 8.844 (s, 1H), 8.096 (s, 1H), 8.014 (s, 1H), 7.877 (d, J=8.7 Hz, 1H), 7.707-7.612 (m, 1H), 7.440-7.395 (m, 2H), 7.211-7.089 (m, 2H), 2.645 (s, 3H). LCMS (M+H): 425.9.

Compound 11: ¹H NMR (300 MHz, CDCl₃-d⁶-DMSO) δ 9.078 (d, J=2.4 Hz, 1H), 8.285 (s, 1H), 8.198 (s, 1H), 7.986 (d, J=9.0 Hz, 1H), 7.800 (dd, J=9.0, 2.1 Hz, 1H), 7.636-7.502 (m, 1H), 7.365-7.276 (m, 2H), 7.224-7.160 (m, 1H), 2.833 (s, 3H). LCMS (M+H): 426.0.

Compound 12: ¹H NMR (300 MHz, CDCl₃-d⁶-DMSO) δ 9.086 (s, 1H), 8.283 (s, 1H), 8.182 (s, 1H), 7.969 (d, J=8.7 Hz, 1H), 7.772 (d, J=9.0 Hz, 1H), 7.573-7.464 (m, 4H), 2.787 (s, 3H). LCMS (M+H): 441.9.

Compound 13: ¹H NMR (300 MHz, CDCl₃-d⁶-DMSO) δ 9.073 (d, J=2.1 Hz, 1H), 8.288 (s, 1H), 8.168 (s, 1H), 7.980 (d, J=9.0 Hz, 1H), 7.790 (ds, J=9.0, 2.1 Hz, 1H), 7.436-7.366 (m, 4H), 3.017 (septet, J=6.9 Hz, 1H), 2.782 (s, 3H), 1.315 (d, J=6.9 Hz, 1H). LCMS (M+2+H): 452.1.

Compound 14: ¹H NMR (300 MHz, CDCl₃-d⁶-DMSO) δ 8.861 (d, J=2.1 Hz, 1H), 8.483 (s, 1H), 8.338 (s, 1H), 7.987 (d, J=9.0 Hz, 1H), 7.933-7.895 (m, 1H), 7.594 (d, J=2.1 Hz, 1H), 7.491-7.417 (m, 2H), 2.549 (s, 3H), 2.026 (s, 3H). ¹³C NMR (75 MHz, CDCl₃-d⁶-DMSO) δ 167.134, 153.372, 147.000, 140.366, 139.994, 136.788, 135.782, 133.121, 131.250, 130.806, 129.584, 127.577, 126.863, 123.789, 121.448, 120.229, 118.324, 16.807, 11.889. LCMS (M+2+H): 458.0.

Compound 15: ¹H NMR (300 MHz, CDCl₃-d⁶-DMSO) δ 9.055 (s, 1H), 8.271 (s, 1H), 8.159 (s, 1H), 7.958 (d, J=9.0 Hz, 1H), 7.775 (d, J=9.0 Hz, 1H), 7.102 (s, 3H), 2.774 (s, 3H), 2.409 (s, 6H). ¹³C NMR (75 MHz, CDCl₃-d⁶-DMSO) δ 167.473, 152.850, 147.207, 138.888, 138.732, 138.557, 138.447, 135.009, 132.364, 130.648, 129.506, 127.700, 123.942, 122.663, 121.567, 120.295, 119.384, 20.782, 12.433. LCMS (M+H): 436.0.

Compound 16: ¹H NMR (400 MHz, CDCl₃-d⁶-DMSO) δ 9.116 (s, 1H), 8.424 (d, J=6.9 Hz, 2H), 8.299 (s, 1H), 8.258 (s, 1H), 7.992 (d, J=6.9 Hz, 1H), 7.803-7.782 (m, 3H), 2.900 (s, 3H). LCMS (M+H): 452.9.

Compound 17: ¹H NMR (300 MHz, CDCl₃-d⁶-DMSO) δ 9.050 (d, J=1.2 Hz, 1H), 8.412 (s, 1H), 8.354 (s, 1H), 8.235 (d, J=8.8 Hz, 1H), 7.885 (d, J=8.8 Hz, 1H), 7.485-7.301 (m, 4H), 2.132 (s, 3H), 2.106 (s, 3H). ¹³C NMR (75 MHz, CDCl₃-d⁶-DMSO) δ 166.676, 151.784, 144.478, 141.207, 140.136, 137.882, 137.586, 135.844, 134.383, 131.153, 129.810, 128.390, 128.333, 127.548, 126.777, 124.489, 122.481, 121.958, 116.565, 17.249, 12.205. LCMS (M+H): 422.0.

Compound 18: ¹H NMR (400 MHz, CDCl₃-d⁶-DMSO) δ 9.048 (d, J=1.8 Hz, 1H), 8.281 (s, 1H), 8.188 (s, 1H), 7.977 (d, J=6.0 Hz, 1H), 7.800 (d, J=6.0, 1.8 Hz, 1H), 7.449 (dd, J=6.0, 6.0 Hz, 1H), 7.099-7.001 (m, 3H), 3.882 (s, 3H), 2.810 (s, 3H). LCMS (M+2+H): 440.1.

Compound 19: ¹H NMR (300 MHz, CDCl₃-d⁶-DMSO) δ 9.814 (d, J=2.1 Hz, 1H), 8.633 (d, J=2.7 Hz, 1H), 8.109 (d, J=2.1 Hz, 1H), 8.082-7.883 (m, 3H), 7.531-7.500 (m, 4H). LCMS (M+H): 394.9.

Compound 20: ¹H NMR (400 MHz, CDCl₃-d⁶-DMSO) δ 9.042 (d, J=1.5 Hz, 1H), 8.284 (s, 1H), 8.220 (s, 1H), 7.984 (d, J=6.9 Hz, 1H), 7.814 (d, J=6.9 Hz, 1H), 7.696 (d, J=6.6 Hz, 2H), 7.472 (d, J=6.6 Hz, 2H), 2.816 (s, 3H). LCMS (M+H): 485.9.

Compound 21: ¹H NMR (400 MHz, CDCl₃-d⁶-DMSO) δ 9.058 (d, J=1.5 Hz, 1H), 8.286 (s, 1H), 8.245 (s, 1H), 7.979 (d, J=6.6 Hz, 1H), 7.801 (dd, J=6.6, 1.5 Hz, 1H), 7.589-7.531 (m, 1H), 7.185-7.117 (m, 2H), 2.680 (s, 3H). LCMS (M+H): 444.0.

Compound 22: ¹H NMR (300 MHz, CDCl₃-CD₃OD) δ 8.906 (s, 1H), 8.095 (s, 1H), 8.014 (s, 1H), 8.031 (s, 1H), 7.747 (d, J=8.7 Hz, 1H), 7.569 (d, J=8.7 Hz, 1H), 7.314 (t, J=7.5 Hz, 1H), 7.181-7.055 (m, 3H), 2.576 (t, J=7.2 Hz, 2H), 2.546 (s, 3H), 1.636-1.561 (m, 2H), 0.876 (t, J=7.2 Hz, 3H). LCMS: 450.0 (M+H), 452.0 (M+2+H).

Compound 23: ¹H NMR (300 MHz, CDCl₃-CD₃OD) δ 8.817 (d, J=1.8 Hz, 1H), 8.207 (s, 1H), 7.992 (s, 1H), 7.933 (d, J=8.7 Hz, 1H), 7.830 (d, J=8.7 Hz, 2H), 7.770-7.733 (m, 1H), 7.684 (d, J=8.7 Hz, 2H), 2.784 (s, 3H). LCMS (M+H): 476.0.

Compound 24: ¹H NMR (300 MHz, CDCl₃-d⁶-DMSO) δ 9.076 (d, J=1.8 Hz, 1H), 8.291 (s, 1H), 8.244 (s, 1H), 7.978 (d, J=8.7 Hz, 1H) 7.787 (dd, J=8.7, 1.8 Hz, 1H), 7.546-7.457 (m, 2H), 7.376-7.291 (m, 2H), 2.682 (s, 3H). LCMS (M+2+H): 428.0.

Compound 25: ¹H NMR (300 MHz, CDCl₃-d⁶-DMSO) δ 9.080 (s, 1H), 8.283 (s, 1H), 8.198 (s, 1H), 7.984 (d, J=8.7 Hz, 1H), 7.798 (dd, J=8.7, 1.8 Hz, 1H), 7.566-7.400 (m, 4H), 2.866 (s, 3H). LCMS (M+H): 441.9.

Compound 26: ¹H NMR (300 MHz, CDCl₃-d⁶-DMSO) δ 9.062 (d, J=1.8 Hz, 1H), 8.283 (s, 1H), 8.175 (s, 1H), 7.979 (d, J=9.0 Hz, 1H), 7.792 (dd, J=9.0, 1.8 Hz, 1H), 7.447-7.270 (m, 4H), 2.785 (s, 3H), 2.459 (s, 3H). LCMS (M+H): 422.0.

Compound 27: ¹H NMR (300 MHz, CDCl₃-d⁶-DMSO) δ 9.078 (d, J=2.1 Hz, 1H), 8.297 (s, 1H), 8.243 (s, 1H), 7.974 (d, J=9.0 Hz, 1H), 7.790 (dd, J=9.0, 2.1 Hz, 1H), 7.627 (dd, J=2.1, 0.4 Hz, 1H), 7.457 (d, J=2.1 Hz, 1H), 7.448 (d, J=0.4 Hz, 1H), 2.631 (s, 3H). LCMS (M+H): 475.9.

Compound 28: ¹H NMR (300 MHz, CDCl₃-d⁶-DMSO) δ 9.071 (d, J=2.1 Hz, 1H), 8.304 (s, 1H), 8.202 (s, 1H), 7.974 (d, J=8.7 Hz, 1H), 7.780 (d, J=8.7, 2.1 Hz, 1H), 7.279-7.209 (m, 2H), 7.107 (s, 1H), 2.605 (s, 3H), 2.389 (s, 3H), 2.055 (s, 3H). ¹³C NMR (75 MHz, CDCl₃-d⁶-DMSO) δ 167.149, 153.000, 147.201, 139.695, 138.712, 137.399, 135.991, 134.715, 132.374, 132.104, 130.677, 130.359, 129.839, 127.634, 123.850, 121.413, 120.206, 118.301, 20.269, 16.276, 11.581. LCMS (M+2+H): 438.1.

Compound 29: ¹H NMR (300 MHz, d⁶-DMSO) δ 8.897 (s, 1H), 8.408-8.303 (m, 3H), 8.140-8.060 (m, 2H), 7.931-7.833 (m, 3H), 2.873 (s, 3H). LCMS (M+H): 452.9.

Compound 30: ¹H NMR (300 MHz, CDCl₃-d⁶-DMSO) δ 9.102 (d, J=2.4 Hz, 1H), 8.489 (s, 1H), 8.433 (d, J=8.7 Hz, 1H), 8.363 (s, 1H), 7.892 (dd, J=8.7, 2.4 Hz, 1H), 7.339 (d, J=7.2 Hz, 1H), 7.261 (dd, J=7.2, 7.2 Hz, 1H), 7.144 (d, J=7.2 Hz, 1H), 2.564 (s, 3H), 2.387 (s, 3H), 1.959 (s, 3H). LCMS (M+H): 436.0.

Compound 31: ¹H NMR (300 MHz, CDCl₃-d⁶-DMSO) δ 9.074 (d, J=2.1 Hz, 1H), 8.296 (s, 1H), 8.220 (s, 1H), 7.971 (d, J=9.0 Hz, 1H), 7.787 (dd, J=9.0, 2.1 Hz, 1H), 7.417 (dd, J=7.8, 2.1 Hz, 1H), 7.342 (d, J=9.0 Hz, 1H), 7.323 (d, J=2.1 Hz, 1H), 2.603 (s, 3H), 2.089 (s, 3H). LCMS (M+H): 456.0.

Compound 32: $^1$H NMR (400 MHz, CDCl$_3$-d$^6$-DMSO) δ 9.086 (d, J=2.0 Hz, 1H), 8.292 (s, 1H), 8.232-8.190 (m, 4H), 7.988 (d, J=9.2 Hz, 1H), 7.800 (dd, J=8.8, 2.0 Hz, 1H), 7.619 (d, J=8.4 Hz, 2H), 7.521 (d, J=8.4 Hz, 1H), 2.594 (s, 3H). LCMS (M+H): 452.0.

Compound 33: $^1$H NMR (300 MHz, CDCl$_3$-d$^6$-DMSO) δ 9.007 (d, J=2.1 Hz, 1H), 8.308 (s, 1H), 8.199 (s, 1H), 8.036 (d, J=9.0 Hz), 7.648 (dd, J=9.0, 2.1 Hz, 1H), 7.429-7.240 (m, 2H), 7.107 (s, 1H), 2.600 (s, 3H), 2.390 (s, 3H), 2.055 (s, 3H). $^{13}$C NMR (75 MHz, CDCl$_3$-d$^6$-DMSO) δ 167.006, 152.391, 146.527, 139.134, 138.231, 136.918, 135.510, 135.005, 131.635, 131.240, 130.018, 129.859, 129.339, 129.267, 127.161, 123.992, 122.967, 120.845, 117.885, 19.788, 15.799, 11.067. LCMS (M+H): 492.1.

Compound 34: $^1$H NMR (300 MHz, CDCl$_3$-d$^6$-DMSO) δ 8.904 (s, 1H), 8.304 (s, 1H), 8.220 (s, 1H), 8.044 (d, J=9.0 Hz, 1H), 7.663 (d, J=9.0 Hz, 1H), 7.435-7.326 (m, 3H), 2.501 (s, 3H), 2.088 (s, 3H). $^{13}$C NMR (75 MHz, CDCl$_3$-d$^6$-DMSO) δ 167.807, 152.968, 147.469, 140.148, 139.635, 138.903, 135.392, 134.755, 132.500, 132.144, 131.574, 130.941, 130.307, 129.927, 129.624, 127.768, 124.865, 123.931, 121.923, 119.164, 16.790, 11.940. LCMS (M+H): 412.1.

Compound 35: $^1$H NMR (400 MHz, CDCl$_3$-d$^6$-DMSO) δ 9.098 (s, 1H), 8.598 (d, J=8.8 Hz, 1H), 8.486 (s, 1H), 8.341 (s, 1H), 8.127 (d, J=8.8 Hz, 1H), 7.771 (d, J=8.8 Hz, 2H), 7.553-7.286 (m, 6H), 2.609 (s, 3H), 2.137 (s, 3H). $^{13}$C NMR (75 MHz, CDCl$_3$-d$^6$-DMSO) δ 167.446, 151.461, 140.679, 139.969, 139.859, 138.030, 136.428, 135.028, 132.011, 131.863, 131.703, 130.941, 130.159, 128.963, 128.573, 128.409, 127.943, 127.358, 126.831, 123.616, 121.662, 17.226, 11.970. LCMS (M+H): 454.1.

Compound 36: $^1$H NMR (300 MHz, CDCl$_3$-CD$_3$OD) δ 8.881 (d, J=2.1 Hz, 1H), 8.250 (s, 1H), 8.089 (s, 1H), 7.920 (d, J=9.0 Hz, 1H), 7.735 (dd, J=9.0, 2.1 Hz, 1H), 7.362-7.311 (m, 1H), 7.232-7.207 (m, 2H), 2.489 (s, 3H), 2.018 (s, 6H). LCMS (M+H): 436.0.

Compound 37: $^1$H NMR (300 MHz, d$^6$-DMSO) δ 9.030 (d, J=1.8 Hz, 1H), 8.304 (s, 1H), 8.247 (s, 1H), 7.963 (d, J=8.7 Hz, 1H), 7.801-7.734 (m, 1H), 7.020 (s, 2H), 2.349 (s, 3H), 2.157 (s, 3H), 1.965 (s, 6H). $^{13}$C NMR (100 MHz, d$^6$-DMSO) δ 176.820, 162.710, 156.831, 149.351, 148.637, 148.296, 145.066, 144.337, 143.855, 141.965, 140.288, 138.098, 137.225, 133.453, 130.974, 129.756, 127.730, 40.068, 30.276, 26.314, 20.663. LCMS (M+H): 450.1.

Compound 38: $^1$H NMR (300 MHz, CDCl$_3$-CD$_3$OD) δ 8.918 (s, 1H), 8.196 (s, 1H), 8.128 (s, 1H), 7.929 (d, J=9.0 Hz, 1H), 7.750 (d, J=9.0 Hz, 1H), 7.527-7.461 (m, 2H), 7.399-7.346 (m, 1H), 7.268 (d, J=7.8 Hz, 1H), 2.537 (s, 3H), 2.413 (q, J=7.2 Hz, 2H), 1.111 (t, J=7.2 Hz, 3H). LCMS (M+2+H): 438.0

Compound 39: $^1$H NMR (300 MHz, d$^6$-DMSO) δ 9.046 (d, J=2.1 Hz, 1H), 8.294 (s, 1H), 8.264 (s, 1H), 7.982 (d, J=8.7 Hz, 1H), 7.802 (dd, J=8.7, 2.1 Hz, 1H), 7.618 (d, J=8.7 Hz, 1H), 7.567-7.536 (m, 1H), 2.653 (s, 3H). LCMS (M+H): 475.8.

Compound 40: $^1$H NMR (300 MHz, d$^6$-DMSO) δ 9.036 (s, 1H), 8.288 (s, 2H), 7.975 (d, J=9.0 Hz, 1H), 7.860-7.792 (m, 1H), 7.405-7.313 (m, 3H), 2.705 (s, 3H). LCMS (M+2+1): 445.9.

Compound 41: $^1$H NMR (300 MHz, d$^6$-DMSO) δ 9.016 (d, J=1.8 Hz, 1H), 8.365 (s, 1H), 8.328 (s, 1H), 7.986 (d, J=9.3 Hz, 1H), 7.840-7.808 (m, 1H), 7.661-7.582 (m, 3H), 2.720 (s, 3H). LCMS (M+H): 475.9.

Compound 42: $^1$H NMR (300 MHz, d$^6$-DMSO) δ 9.020 (s, 1H), 8.360 (s, 1H), 8.314 (s, 1H), 7.929 (d, J=9.0 Hz, 1H), 7.810 (d, J=9.0 Hz, 1H), 7.704 (s, 2H), 2.604 (s, 3H). LCMS (M+2+H): 511.9.

Compound 43: $^1$H NMR (300 MHz, d$^6$-DMSO) δ 9.213 (s, 1H), 8.974 (s, 1H), 8.432 (s, 1H), 8.416 (s, 1H), 7.994-7.837 (m, 3H), 7.810 (d, J=2.4 Hz, 1H), 7.541-7.490 (m, 2H), 7.368-7.319 (m, 1H). $^{13}$C NMR (100 MHz, d$^6$-DMSO) δ 176.623, 160.721, 156.801, 149.028, 148.778, 144.743, 142.174, 140.292, 138.682, 137.267, 136.094, 136.018, 134.124, 133.809, 130.496, 130.026, 128.037. LCMS (M+H): 394.0.

Compound 44: $^1$H NMR (300 MHz, CDCl$_3$-CD$_3$OD) δ 8.966 (d, J=1.8 Hz, 1H), 8.211 (s, 1H), 8.183 (s, 1H), 8.168 (d, J=9.0 Hz, 1H), 8.012 (dd, J=9.0, 1.8 Hz, 1H), 7.784-7.753 (m, 2H), 7.514-7.464 (m, 2H), 7.418-7.389 (m, 1H), 7.304-7.264 (m, 2H), 7.132 (s, 1H), 2.575 (s, 3H), 2.405 (s, 3H), 2.037 (s, 3H). LCMS (M+H): 434.1.

Compound 45: $^1$H NMR (400 MHz, d$^6$-DMSO) δ 8.99 (d, J=2.4 Hz, 1H), 8.71 (s, 1H), 8.23~8.20 (m, 2H), 8.12 (d, J=8.8 Hz, 2H), 8.04 (dd, J=8.8, 2.4 Hz, 2H), 7.70~7.67 (m, 3H), 2.85 (s, 3H). LCMS (M+H)=407.9.

Compound 46: $^1$H NMR (400 MHz, d$^6$-DMSO) δ 8.97 (d, J=2.0 Hz, 1H), 8.34 (s, 1H), 8.04~7.95 (m, 5H), 7.54~7.52 (m, 4H), 2.84 (s. 3H). LCMS (M+H)=424.9.

Compound 47: $^1$H NMR (400 MHz, CD$_3$OD) δ 8.64 (d, J=2.4 Hz, 1H), 7.94 (s, 1H), 7.88 (d, J=8.8 Hz, 1H), 7.76 (dd, J=8.8, 2.4 Hz, 1H), 7.54~7.51 (m, 2H), 7.46 (t, J=8.0 Hz, 2H), 7.39~7.34 (m, 1H), 6.89 (d, J=4.0 Hz, 1H), 6.31 (d, J=8.8 Hz, 1H), 4.00 (s. 3H). LCMS (M+H)=406.9.

Compound 48: $^1$H NMR (400 MHz, CD$_3$OD) δ 8.63 (d, J=2.4 Hz, 1H), 7.89~7.86 (m, 2H), 7.74 (dd, J=8.8, 2.4 Hz, 1H), 7.56~7.51 (m, 2H), 7.44~7.40 (m, 2H), 6.89 (d, J=2.8 Hz, 1H), 6.77 (d, J=2.8 Hz, 1H), 2.55 (s. 3H). LCMS (M+2+H)=408.9.

Compound 49: $^1$H NMR (400 MHz, d$^6$-DMSO) δ 9.19 (d, J=2.0 Hz, 1H), 8.17 (s, 1H), 7.99 (d, J=9.2 Hz, 1H), 7.87~7.83 (m, 3H), 7.64~7.56 (m, 3H), 2.63 (s. 3H). LCMS (M+2+H)=410.9.

Compound 50: $^1$H NMR (400 MHz, d$^6$-DMSO) δ 8.510 (dd, J=12.0, 2.8 Hz, 1H), 8.315 (s, 1H), 8.088 (s, 1H), 8.011-7.974 (m, 1H), 7.619-7.569 (m, 1H), 7.339 (d, J=8.0 Hz, 1H), 7.280 (d, J=8.0 Hz, 1H), 7.203 (s, 1H). 2.527 (s, 3H), 2.332 (s, 3H), 1.908 (s, 3H). LCMS (M+2+H)=376.0.

Compound 51: $^1$H NMR (400 MHz, d$^6$-DMSO) δ 9.02 (d, J=2.0 Hz, 1H), 8.40 (s, 1H), 7.94 (s, 1H), 7.83 (d, J=8.8 Hz, 1H), 7.76 (dd, J=8.8, 2.0 Hz, 1H), 7.63~7.51 (m, 5H), 2.74 (s. 3H). LCMS (M+H)=407.9.

Compound 52: $^1$H NMR (400 MHz, CD$_3$OD) δ 8.70 (d, J=2.4 Hz, 1H), 8.04~8.01 (m, 2H), 7.95 (d, J=8.8 Hz, 1H), 7.82 (dd, J=8.8, 2.4 Hz, 1H), 7.67~7.63 (m, 2H), 7.59~7.54 (m, 1H), 7.49~7.46 (m, 2H), 7.21~7.13 (m, 2H), 7.08~7.06 (m, 1H), 2.54 (s. 3H). LCMS (M+2+H)=458.9.

Compound 53: $^1$H NMR (300 MHz, d$^6$-DMSO) δ 9.06 (s, 1H), 8.49 (s, 1H), 8.08~8.05 (m, 2H), 7.97 (d, J=8.7 Hz, 1H), 7.76 (dd, J=8.7, 1.5 Hz, 1H), 7.57~7.55 (m, 3H), 2.98 (s. 3H). LCMS (M+2+H)=410.9.

Compound 54: $^1$H NMR (400 MHz, d$^6$-DMSO) δ 8.99 (d, J=2.4 Hz, 1H), 8.68 (s, 1H), 8.05 (d, J=8.8 Hz, 1H), 7.95 (dd, J=8.8, 2.4 Hz, 1H), 7.63 (m, 2H), 7.54 (t, J=8.0 Hz, 2H), 7.44 (t, J=7.6 Hz, 1H), 2.66 (s. 3H). LCMS (M+2+H)=409.9.

Compound 55: $^1$H NMR (400 MHz, CD$_3$OD) δ 8.70 (d, J=2.0 Hz, 1H), 7.94~7.90 (m, 2H), 7.79 (dd, J=8.8, 2.0 Hz, 1H), 7.46 (d, J=7.2 Hz, 2H), 7.40 (t, J=8.0 Hz, 2H), 7.29~7.25 (m, 2H), 2.81 (s. 3H). LCMS (M+2+H)=410.0.

Compound 56: ¹H NMR (400 MHz, d⁶-DMSO) δ 9.02 (d, J=2.0 Hz, 1H), 8.79 (s, 1H), 8.07 (d, J=9.2 Hz, 1H), 8.00~7.93 (m, 4H), 2.87 (s. 3H). LCMS (M+H)=476.8.

Compound 57: ¹H NMR (300 MHz, CDCl₃-d⁶-DMSO) δ 8.756 (d, J=1.8 Hz, 1H), 8.194 (s, 1H), 7.955-7.905 (m, 2H), 7.784-7.747 (m, 1H), 7.491 (s, 3H), 2.786 (s, 3H). LCMS (M+H): 475.8.

Compound 58: ¹H NMR (400 MHz, d⁶-DMSO) δ 8.979 (d, J=2.4 Hz, 1H), 8.413 (s, 1H), 8.199 (d, J=2.0 Hz, 1H), 8.072 (s, 1H), 7.340 (d, J=8.0 Hz, 1H), 7.282 (d, J=7.6 Hz, 1H), 7.216 (s, 1H), 2.672 (d, J=1.6 Hz, 3H), 2.353 (s, 3H), 1.908 (s, 3H). LCMS (M+H): 513.9.

Compound 59: ¹H NMR (400 MHz, d⁶-DMSO) δ 8.744 (s, 1H), 8.364 (s, 1H), 8.051 (s, 1H), 7.694 (s, 1H), 7.335 (d, J=8.0 Hz, 1H), 7.278 (d, J=8.0 Hz, 1H), 7.197 (s, 1H), 2.698 (s, 3H), 2.557 (s, 3H), 2.350 (s, 3H), 1.984 (s, 3H). LCMS (M+H): 449.9.

Compound 60: ¹H NMR (400 MHz, d⁶-DMSO) δ 9.144 (s, 1H), 8.311 (s, 1H), 7.990 (s, 1H), 7.905 (d, J=8.8 Hz, 1H), 7.697 (d, J=8.8 Hz, 1H), 7.329 (d, J=8.0 Hz, 1H), 7.274 (d, J=8.0 Hz, 1H), 7.187 (s, 1H), 2.522 (s, 3H), 2.347 (s, 3H), 1.960 (s, 3H). LCMS (M+H): 483.9.

Compound 61: ¹H NMR (400 MHz, d⁶-DMSO) δ 8.99 (d, J=2.0 Hz, 1H), 8.65 (s, 1H), 8.06 (d, J=8.8 Hz, 1H), 8.01 (dd, J=8.8, 2.0 Hz, 1H), 7.90~7.87 (m, 2H), 7.67~7.64 (m, 3H), 3.91 (s. 3H). LCMS (M+2+H)=409.9.

Compound 62: ¹H NMR (400 MHz, CD₃OD) δ 8.62 (d, J=2.0 Hz, 1H), 7.95 (s, 1H), 7.84 (d, J=8.8 Hz, 1H), 7.74 (dd, J=8.8, 2.0 Hz, 1H), 7.21 (d, J=7.6 Hz, 1H), 7.14 (t, J=7.6 Hz, 1H), 7.01 (s, 1H), 6.92 (d, J=3.6 Hz, 1H), 6.12 (d, J=3.6 Hz, 1H), 3.80 (s. 3H), 2.35 (s, 3H), 2.19 (s, 3H). LCMS (M+H)=434.9.

Compound 63: ¹H NMR (300 MHz, CDCl₃-d⁶-DMSO) δ 9.081 (s, 1H), 8.478 (s, 1H), 7.861 (d, J=8.7 Hz, 1H), 7.582 (dd, J=12.0, 2.1 Hz, 1H), 7.276-7.110 (m, 3H), 2.528 (s, 3H), 2.387 (s, 3H), 2.068 (s, 3H). LCMS (M+H): 452.0.

Compound 73: ¹H NMR (400 MHz, CDCl₃-d⁶-DMSO) δ 9.107 (d, J=2.0 Hz, 1H), 8.284 (s, 1H), 8.246 (s, 1H), 8.041 (d, J=9.2 Hz, 1H), 7.972 (d, J=8.0 Hz, 1H), 7.899 (d, J=8.0 Hz, 1H), 7.837 (dd, J=9.2, 2.4 Hz, 1H), 7.532-7.494 (m, 1H), 7.431-7.393 (m, 1H), 3.347 (s, 3H). LCMS (M+H): 465.0.

Compound 74: ¹H NMR (400 MHz, CDCl₃-d⁶-DMSO) δ 9.102 (d, J=2.0 Hz, 1H), 8.276 (d, J=1.6 Hz, 1H), 8.025 (s, 1H), 8.021-7.994 (m, 2H), 7.815 (dd, J=8.8, 2.0 Hz, 1H), 7.355 (s, 3H), 3.148 (s, 3H), 2.589 (s, 3H). LCMS (M+H): 491.0.

Compound 75: ¹H NMR (300 MHz, CDCl₃-d⁶-DMSO) δ 9.105 (d, J=2.1 Hz, 1H), 8.359 (d, J=9.0 Hz, 1H), 8.313 (s, 1H), 8.248 (s, 1H), 8.125-8.004 (m, 3H), 7.908 (d, J=9.0 Hz, 1H), 7.838-7.756 (m, 2H), 7.628-7.573 (m, 1H), 3.271 (s, 3H). LCMS (M+H): 459.0.

Compound 76: ¹H NMR (400 MHz, d⁶-DMSO) δ 9.16 (d, J=2.0 Hz, 1H), 7.90 (d, J=8.8 Hz, 1H), 7.80 (dd, J=8.8, 2.0 Hz, 1H), 7.72 (s, 1H), 7.28~7.49 (m, 8H), 2.14 (s. 3H). LCMS (M+H)=417.9.

Compound 77: ¹H NMR (400 MHz, dDMSO): 8.39 (s, 1H), 8.34 (s, 1H), 8.19 (s, 1H), 8.19 (d, J=8.4 Hz, 1H), 7.63-7.46 (m, 6H), 2.75 (s, 6H). LCMS [M+1]⁺: 344.1.

Compound 78: ¹H NMR (400 MHz, CDCl₃): 8.49 (s, 1H), 8.18 (s, 1H), 8.14 (s, 1H), 8.04 (d, J=8.4 Hz, 1H), 7.60-7.44 (m, 6H), 4.08 (s, 3H), 2.80 (s, 3H), 2.58 (s, 3H). LCMS [M+H]⁺: 358.2.

Compound 79: ¹H NMR (400 MHz, CDCl₃): 8.80 (s, 1H), 8.29 (s, 1H), 8.26 (s, 1H), 8.18 (s, 1H), 7.82 (d, J=8.8 Hz, 1H), 7.73 (s, 1H), 7.70 (s, 1H), 7.61-7.52 (m, 6H), 5.12 (s, 2H), 4.72 (s, 2H), 4.10 (s, 3H). LCMS [M+1]⁺: 516.0.

Compound 80: ¹H NMR (400 MHz, CDCl₃): 8.93 (s, 1H), 8.35 (s, 1H), 8.21 (d, J=8.4 Hz, 2H), 8.03 (s, 1H), 7.88 (d, J=8.8 Hz, 1H), 7.76 (d, J=8.4 Hz, 2H), 7.66 (d, J=9.2 Hz, 1H), 4.65 (s, 2H). LCMS [M]⁺: 425.0

Compound 81: ¹H NMR (400 MHz, d⁶-DMSO): δ 7.42 (t, J=7.6 Hz, 1H); 7.52 (t, J=7.2 Hz, 2H); 7.78 (d, J=7.2 Hz, 2H); 7.88 (d, J=8.4 Hz, 1H); 7.96 (dd, J=8.8, 2.0 Hz, 1H); 8.09 (d, 8.8 Hz, 1H); 8.39 (d, J=8.4 Hz, 1H); 8.52 (s, 1H); 8.97 (d, J=2.0 Hz, 1H); LCMS [M+1]⁺: 405.0.

Compound 82: ¹H NMR (300 MHz, d⁶-DMSO): δ 7.43 (t, J=7.5 Hz, 1H); 7.53 (t, J=8.1 Hz, 2H); 7.68 (t, J=7.5 Hz, 1H); 7.79-7.86 (m, 3H); 7.99 (dd, J=9.0, 1.8 Hz, 1H); 8.15 (d, J=9.0, 2.0 Hz, 1H); 8.29 (d, J=8.1 Hz, 1H); 8.52 (m, 1H); 8.65 (s, 1H); 8.93 (d, J=1.8 Hz, 1H); LCMS [M+1]⁺: 405.0.

Compound 83: ¹H NMR (400 MHz, d⁶-DMSO): δ 7.08 (m, 1H); 7.33 (t, J=7.2 Hz, 1H); 7.52 (t, J=8.0 Hz, 2H) 7.58 (t, J=2.8 Hz, 1H); 7.77 (d, J=7.6 Hz, 2H); 7.89 (dd, J=8.8, 2.0 Hz, 1H); 7.97 (d, J=8.8 Hz, 1H); 8.42 (m, 1H); 8.47 (m, 1H); 8.83 (d, J=2.0 Hz, 1H); LCMS [M+1]⁺: 394.0.

Compound 84: ¹H NMR (300 MHz, d⁶-DMSO): δ 2.26 (s, 3H); 2.34 (s, 3H); 7.07-7.10 (m, 2H); 7.17 (d, J=8.4 Hz, 1H) 7.48 (d, J=8.7 Hz, 2H); 7.83 (dd, J=9.0, 2.1 Hz, 1H); 8.02 (d, 9.0 Hz, 1H); 8.17-8.23 (m, 3H); 8.74 (d, J=2.1 Hz, 1H); LCMS [M+1]⁺: 433.1.

Compound 85: LCMS [M]⁺: 436.3.
Compound 86: LCMS [M]⁺: 407.3.
Compound 87: LCMS [M]⁺: 395.2.
Compound 88: LCMS [M]⁺: 396.2.
Compound 89: LCMS [M]⁺: 411.3.
Compound 90: LCMS [M]⁺: 409.2.
Compound 91: LCMS [M]⁺: 425.3.
Compound 92: LCMS [M]⁺: 396.2.

Example 3

In Vitro Anti-Influenza Virus Assay (Neutralization Test)

Anti-influenza activities of the quinoline compounds were evaluated by measuring the ability of a test compound to inhibit the cytopathic effect induced by an influenza virus on MDCK cells. The 96-well tissue culture plates were seeded with 200 μL of MDCK cells at a concentration of $1.1 \times 10^5$ cells/mL in DMEM with 10% fetal bovine serum (FBS). The plates were incubated for 24-30 h at 37° C. and were used at about 90% confluency. Influenza A/WSN/33 ($H_1N_1$) virus (100 $TCID_{50}$) was added to the cells and incubated at 35° C. for 1 h. After adsorption, the infected cell plates were overlaid with 50 μL of DMEM plus 2% FBS and a test compound with different concentrations. The plate was incubated at 35° C. for 72 h. At the end of incubation, the plates were fixed by the addition of 100 μL of 4% formaldehyde for 1 h at room temperature. After the removal of formaldehyde, the plates were stained with 0.1% crystal violet for 15 min at room temperature. The plates were washed and dried, and the density of the well was measured at 570 nm. The concentration required for a test compound to reduce the virus-induced cytopathic effect (CPE) by 50% relative to the virus control was expressed as $IC_{50}$.

Compounds 1-63 and 73-76 were tested. Unexpectedly, Compounds 29, 39-41, and 43 showed $IC_{50}$ values between 6 μM and 25 μM; Compounds 3, 6-8, 11, 12, 16, 18, 19, 21, 23, 36-38, 42, 46, 48-50, 57-59, and 73-76 showed $IC_{50}$ values between 1 μM and 5.9 μM; and Compounds 4, 5, 9, 10, 13-15, 17, 20, 22, 24-28, 30, 31, 33, 34, 47, 51, and 60 showed $IC_{50}$ values between 10 nM and 0.999 μM.

Compound 28 was also tested on various influenza virus strains. Amantadine or Relenza was also tested for comparison. $IC_{50}$ results are shown in Table 1 below. $IC_{50}$ is defined as the concentration required for a test compound to reduce the virus-induced cytopathic effect (CPE) by 50% relative to the virus control. Unexpectedly, Compound 28 exhibited similar or greater anti-influenza activities, as compared to Amantadine or Relenza.

TABLE 1

| | $IC_{50}$ (μM) | | |
|---|---|---|---|
| Virus strain | Compound 28 | Amantadine | Relenza |
| Influenza A/TW/355/97 (H1N1) | 0.088 ± 0.019 | 12.610 ± 6.928 | 1.046 ± 0.458 |
| Influenza A/TW/147/09 (H1N1) | 0.065 ± 0.001 | 1.472 ± 0.603 | 22.468 ± 3.470 |
| Influenza A/TW/70058/09 (H1N1) | 0.075 ± 0.005 | 0.762 ± 0.280 | 0.860 ± 0.360 |
| Influenza A/TW/70066/09 (H1N1) | 0.074 ± 0.003 | 0.960 ± 0.317 | 0.809 ± 0.150 |

Example 4

In Vitro EV 71, Coxsackie Virus B3, and Human Rhinovirus 2 Neutralization Assay

This assay measured the ability of a test compound to inhibit the cytopathic effect induced by a picornavirus (EV71, Coxsackie Virus B3, or human rhinovirus 2) on RD cells. The method used for this assay is described in Chang et al., *J Med Chem*, 2005, 48(10), 3522-3535. More specifically, 96-well tissue culture plates were seeded with 200 μL of RD cells at a concentration of $3 \times 10^5$ cells/mL in DMEM with 10% FBS. The plates were incubated for 24-30 h at 37° C. and were used at about 90% confluency. Virus (100 TCID50) mixed with different concentrations of a test compound was added to the cells and incubated at 37° C. for 1 h. After adsorption, the infected cell plates were overlaid with 50 μL of DMEM plus 5% FBS and 2% DMSO. The plate was wrapped in Parafilm and incubated at 37° C. for 64 h. At the end of incubation, the plates were fixed by the addition of 100 μL of 0.5% glutaraldehyde for 1 h at room temperature. After the removal of glutaraldehyde, the plates were stained with 0.1% crystal violet for 15 min at room temperature. The plates were washed and dried, and the density of the well was measured at 570 nm. The concentration required for a test compound to reduce the virus-induced cytopathic effect (CPE) by 50% relative to the virus control is expressed as $IC_{50}$.

Compound 28 was tested. Amantadine and Relenza were also tested for comparison. Results are shown in Table 2 below. Unexpectedly, Compound 28 exhibited much greater inhibition of cytopathic effect induced by picornaviruses, as compared to Amantadine or Relenza.

TABLE 2

| | $IC_{50}$ (μM) | | |
|---|---|---|---|
| Virus | Compound 28 | Amantadine | Relenza |
| Enterovirus 71/4643/MP4 | 0.029 ± 0.001 | >25 | >25 |
| Coxsackie B virus 3 | 0.062 ± 0.002 | >25 | >25 |
| Human rhinovirus 2 | 0.079 ± 0.002 | >25 | >25 |

Example 5

In Vitro HSV-1 Plaque Reduction Assay

The method used for this assay is described in Su et al., *Antiviral Res.*, 2008, 79(1), 62-70.

Vero cells were seeded onto a 96-well culture plate at a concentration of $10^4$ cells per well one day before infection. Next day, medium was removed and 10 plaque forming unit (pfu) HSV-1 suspension per well were added and incubated at 37° C. with 5% $CO_2$ for 1 h. The infected cell monolayer was then washed with phosphate buffered saline (PBS) and cultured in maintenance medium containing 1 μM of compounds. After 72 h of incubation at 37° C., cell monolayer was fixed with 10% formalin and stained with 1% crystal violet. Compounds protecting more than 50% of cells from lysis by HSV infection were considered to possess antiviral activity and were further analyzed.

Plaque assays were performed with monolayer cultures of Vero cells in 24-well culture plates. For plaque reduction assay, cell monolayer was infected with virus (50 pfu/well) and incubated at 37° C. with 5% $CO_2$ for 1 h. The infected cell monolayer was then washed three times with PBS and overlaid with overlapping solution (maintenance medium containing 1% methylcellulose and various concentrations of indicated compounds). After 72 h of incubation at 37° C., cell monolayer was fixed with 10% formalin and stained with 1% crystal violet. Plaques were counted and the percentage of inhibition was calculated as $[100-(V_D/V_C)] \times 100\%$, where $V_D$ and $V_C$ refer to the virus titer in the presence and absence of the compound, respectively. The minimal concentration of compounds required to reduce 50% of plaque numbers ($EC_{50}$) was calculated by regression analysis of the dose-response curves generated from plaque assays.

Compound 28 was tested and unexpectedly showed an $EC_{50}$ value less than 10 μM.

Example 6

Inhibition of HIV-1 Replication in Peripheral Blood Mononuclear Cells

Equal amounts of wild-type and mutant viruses were used to infect $5 \times 10^4$ peripheral blood mononuclear cells (PBMC) in 1.5 mL medium containing DMSO or various concentrations of a test compound. A half-milliliter of the culture medium was collected from each culture at days 3, 5, and 7. Viral RNA was extracted from the collected culture supernatants and the viral titers (copies/mL) were determined by real-time PCR. The percentage of inhibition was calculated as $[100-(V_D/V_C)] \times 100\%$, where $V_D$ and $V_C$ refer to the virus titers in the presence and absence of the test compound, respectively.

Compounds 14 and 28 were tested in this assay. Unexpectedly, both showed inhibition of HIV replication. AZT (also known as zidovudine) was also tested for comparison. Results are shown in Table 3 below.

TABLE 3

| Compound (concentration)[a] | Inhibition (%) | | |
|---|---|---|---|
| | Day 3 | Day 5 | Day 7 |
| Compound 14 (10 μM) | 20 | 59 | 86 |
| Compound 14 (0.01 μM) | N/A | 48 | N/A |
| Compound 28 (10 μM) | 13 | 79 | 79 |
| Compound 28 (0.01 μM) | NA | 57 | 19 |
| AZT (0.04 μM) | 30 | 60 | 67 |

[a]All tested compounds showed $CC_{50}$ values (50% cytotoxicity concentration) higher than 1.25 μM.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (I):

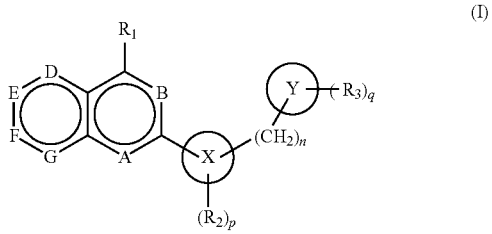

wherein A is N;
each of B, D, E, F, and G, independently, is CR, R being H, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, cyano, amino, hydroxy, alkoxy, aryloxy, $C(O)R_a$, $C(O)OR_a$, $C(O)NR_aR_b$, $C(S)R_a$, $C(NR_a)R_b$, $NR_aR_b$, or $NR_aCONR_bR_c$, in which each of $R_a$, $R_b$, and $R_c$, independently, is H, alkyl, alkenyl, alkynyl, hydroxy, alkoxy, aryloxy, amino, cycloalkyl, cycloalkenyl, heterocycloalkyl, heterocycloalkenyl, aryl, or heteroaryl;
$R_1$ is alkoxy, $C(O)R_d$, $C(O)OR_d$, $CONR_dR_e$, $SO_2R_d$, or CN, in which each of $R_d$ and $R_e$, independently, is H, alkyl, alkenyl, alkynyl, hydroxy, alkoxy, aryloxy, amino, cycloalkyl, cycloalkenyl, heterocycloalkyl, heterocycloalkenyl, aryl, or heteroaryl;
each of $R_2$ and $R_3$, independently, is optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, cyano, amino, hydroxy, alkoxy, aryloxy, $C(O)R_f$, $C(O)OR_f$, $C(O)NR_f$-$R_g$, $C(S)R_f$, $C(NR_f)R_g$, $NR_fR_g$, or $NR_fCONR_gR_h$, in which each of $R_f$, $R_g$, and $R_h$, independently, is H, alkyl, alkenyl, alkynyl, hydroxy, alkoxy, aryloxy, amino, cycloalkyl, cycloalkenyl, heterocycloalkyl, heterocycloalkenyl, aryl, or heteroaryl;

X is

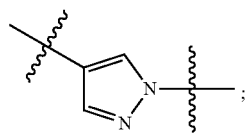 [SMILES: *c1cnn(*)c1]

Y is arylene or a heteroarylene having 1-4 heteroatoms independently selected from the group consisting of N, S, and O;
n is 0, 1, 2, 3, 4, or 5;
p is 1, 2, 3, or 4; and
q is 0, 1, 2, 3, 4, 5, 6, or 7.

2. The compound of claim 1, wherein A is N and each of B, D, E, F, and G is CR.

3. The compound of claim 2, wherein n is 0.

4. The compound of claim 1, wherein Y is phenyl.

5. The compound of claim 1, wherein the compound is selected from the group consisting of

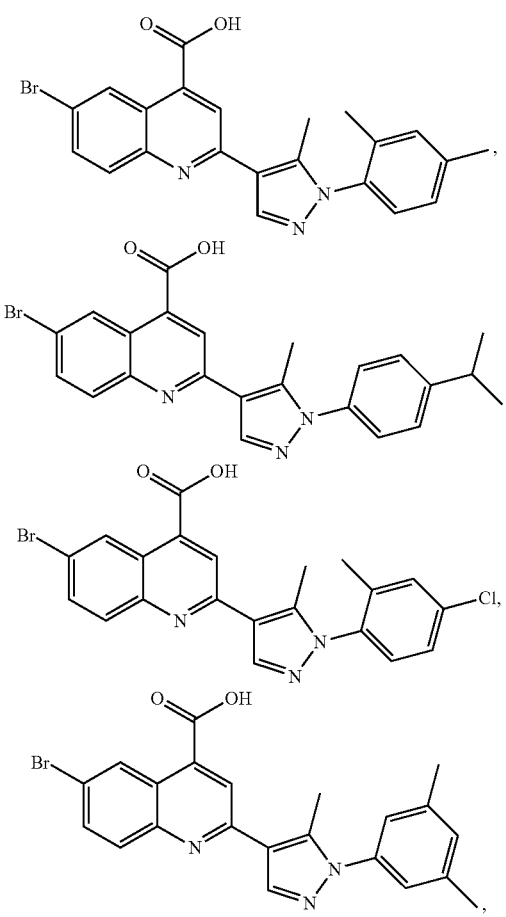

-continued
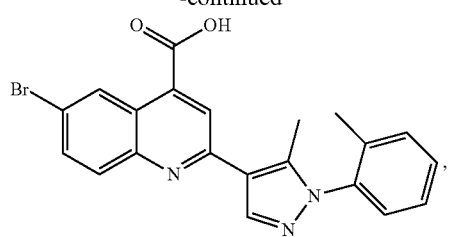
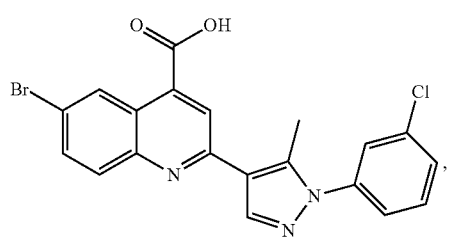
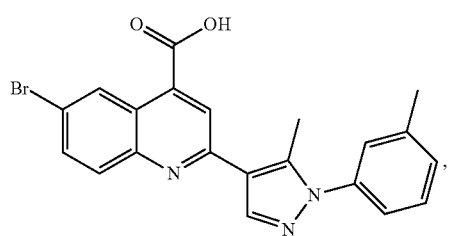
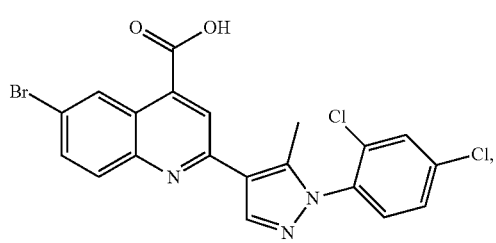
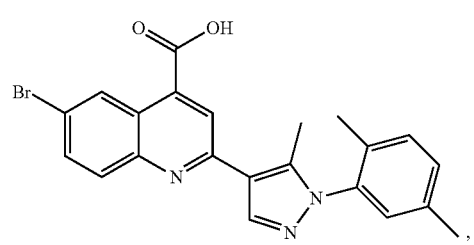
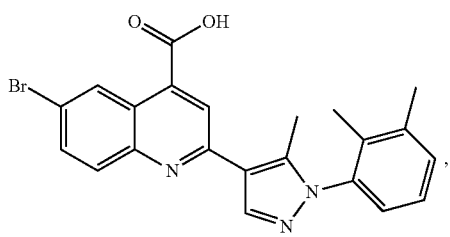
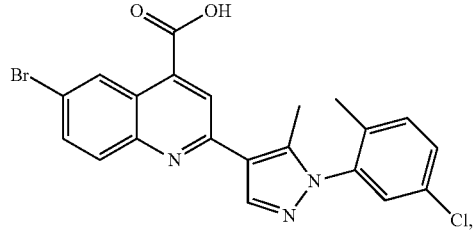
6. A compound selected from the group consisting of
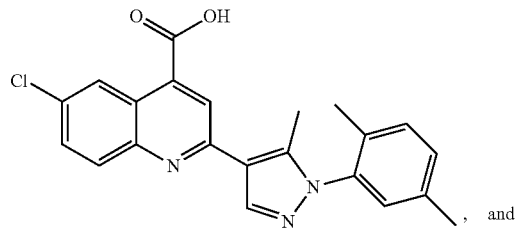

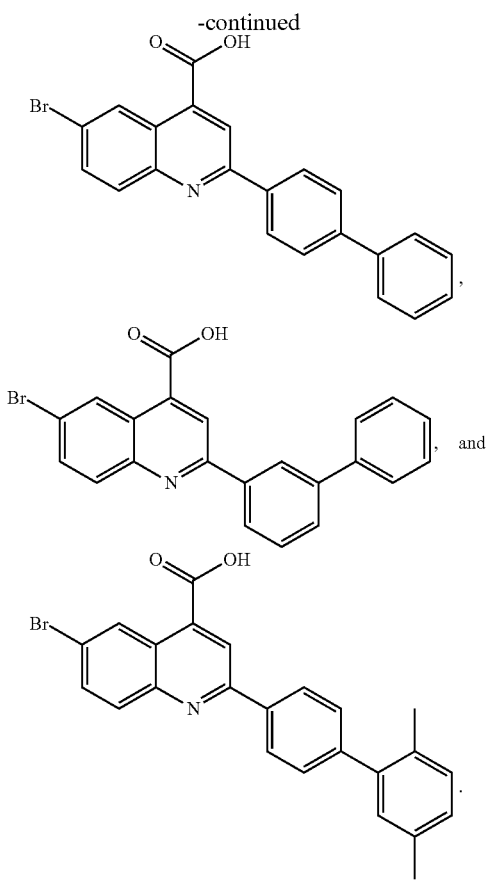

,

7. A method for treating an infection with a virus, comprising administering to a subject in need thereof an effective amount of a compound of formula (I):

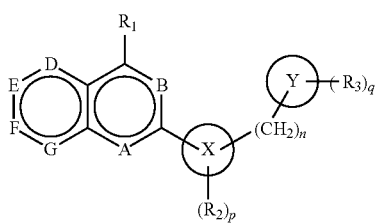

wherein A is N;
each of B, D, E, F, and G, independently, is CR, R being H, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, cyano, amino, hydroxy, alkoxy, aryloxy, $C(O)R_a$, $C(O)OR_a$, $C(O)NR_aR_b$, $C(S)R_a$, $C(NR_a)R_b$, $NR_aR_b$, or $NR_aCONR_bR_c$, in which each of $R_a$, $R_b$, and $R_c$, independently, is H, alkyl, alkenyl, alkynyl, hydroxy, alkoxy, aryloxy, amino, cycloalkyl, cycloalkenyl, heterocycloalkyl, heterocycloalkenyl, aryl, or heteroaryl;
$R_1$ is alkoxy, $C(O)R_d$, $C(O)OR_d$, $CONR_dR_e$, $SO_2R_d$, or CN, in which each of $R_d$ and $R_e$, independently, is H, alkyl, alkenyl, alkynyl, hydroxy, alkoxy, aryloxy, amino, cycloalkyl, cycloalkenyl, heterocycloalkyl, heterocycloalkenyl, aryl, or heteroaryl;
each of $R_2$ and $R_3$, independently, is optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, cyano, amino, hydroxy, alkoxy, aryloxy, $C(O)R_f$, $C(O)OR_f$, $C(O)NR_fR_g$, $C(S)R_f$, $C(NR_f)R_g$, $NR_fR_g$, or $NR_fCONR_gR_h$, in which each of $R_f$, $R_g$, and $R_h$, independently, is H, alkyl, alkenyl, alkynyl, hydroxy, alkoxy, aryloxy, amino, cycloalkyl, cycloalkenyl, heterocycloalkyl, heterocycloalkenyl, aryl, or heteroaryl;
X is

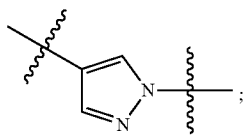 [SMILES: *c1cnn(*)c1]

Y is arylene or a heteroarylene having 1-4 heteroatoms independently selected from the group consisting of N, S, and O;
n is 0, 1, 2, 3, 4, or 5;
p is 1, 2, 3, or 4; and
q is 0, 1, 2, 3, 4, 5, 6, or 7.

8. The method of claim 7, wherein the virus is influenza virus, human rhinovirus 2, enterovirus 71, Coxsackie Virus B3, or Human Immunodeficiency Virus.

9. The method of claim 8, wherein the virus is influenza virus.

10. The method of claim 8, wherein the virus is influenza virus, human rhinovirus 2, enterovirus 71, Coxsackie Virus B3, or Human Immunodeficiency Virus.

11. The method of claim 9, wherein the virus is influenza virus.

12. A pharmaceutical composition comprising a pharmaceutically acceptable carrier and a compound of formula (I):

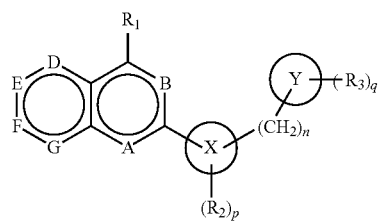

wherein A is N;
each of B, D, E, F, and G, independently, is CR, R being H, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, cyano, amino, hydroxy, alkoxy, aryloxy, $C(O)R_a$, $C(O)OR_a$, $C(O)NR_aR_b$, $C(S)R_a$, $C(NR_a)R_b$, $NR_aR_b$, or $NR_aCONR_bR_c$, in which each of $R_a$, $R_b$, and $R_c$, independently, is H, alkyl, alkenyl, alkynyl, hydroxy, alkoxy, aryloxy, amino, cycloalkyl, cycloalkenyl, heterocycloalkyl, heterocycloalkenyl, aryl, or heteroaryl;

$R_1$ is alkoxy, $C(O)R_d$, $C(O)OR_d$, $CONR_dR_e$, $SO_2R_d$, or CN, in which each of $R_d$ and $R_e$, independently, is H, alkyl, alkenyl, alkynyl, hydroxy, alkoxy, aryloxy, amino, cycloalkyl, cycloalkenyl, heterocycloalkyl, heterocycloalkenyl, aryl, or heteroaryl;

each of $R_2$ and $R_3$, independently, is optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, cyano, amino, hydroxy, alkoxy, aryloxy, $C(O)R_f$, $C(O)OR_f$, $C(O)NR_f$ $R_g$, $C(S)R_f$, $C(NR_f)R_g$, $NR_fR_g$, or $NR_fCONR_gR_h$, in which each of $R_f$, $R_g$, and $R_h$, independently, is H, alkyl, alkenyl, alkynyl, hydroxy, alkoxy, aryloxy, amino, cycloalkyl, cycloalkenyl, heterocycloalkyl, heterocycloalkenyl, aryl, or heteroaryl;

X is

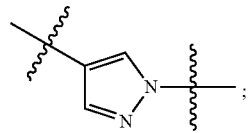 [SMILES: *c1cnn(*)c1]

Y is arylene or a heteroarylene having 1-4 heteroatoms independently selected from the group consisting of N, S, and O;

n is 0, 1, 2, 3, 4, or 5;

p is 1, 2, 3, or 4; and q is 0, 1, 2, 3, 4, 5, 6, or 7.

\* \* \* \* \*

UNITED STATES PATENT AND TRADEMARK OFFICE
CERTIFICATE OF CORRECTION

Page 1 of 2

PATENT NO.      : 8,710,079 B2
APPLICATION NO. : 13/091895
DATED           : April 29, 2014
INVENTOR(S)     : Hsing-Pang Hsieh et al.

It is certified that error appears in the above-identified patent and that said Letters Patent is hereby corrected as shown below:

In the Specification

At column 2, line 9, please change "Pharm Pharm" to --Pharm--.

At column 2, line 12, please change "Ukranica" to --Ukrainica--.

At column 4, line 15, please change "monvalent" to --monovalent--.

At column 23, line 48, please change "M. Fieser, Fieser" to --M. Fieser,--.

At column 24, lines 32-33, please change "Poxyiridae," to --Poxviridae,--.

At column 24, line 41, please change "aminocapronic" to --aminocaproic--.

At column 24, line 48, please change "flutimide)," to --flutamide),--.

At column 26, line 61, please change "167.890. 153.419," to --167.890, 153.419,--.

At column 29, line 54, please change "438.0" to --438.0.--.

At column 30, line 42, please change "DMSO" to --DMSO)--.

At column 31, line 57, please change "dDMSO):" to --$d^6$-DMSO): δ--.

At column 31, line 60, please change "CDCl$_3$):" to --CDCl$_3$): δ--.

At column 31, line 64, please change "CDCl$_3$):" to --CDCl$_3$): δ--.

At column 32, line 1, please change "CDCl$_3$):" to --CDCl$_3$): δ--.

At column 32, line 4, please change "425.0" to --425.0.--.

At column 32, line 8, please change "8.8" to --J=8.8 δ--.

At column 32, line 24, please change "9.0" to --J=9.0--.

At column 32, line 47, please change "(H$_1$N$_1$):" to --(H1N1)--.

Signed and Sealed this
Sixteenth Day of December, 2014

Michelle K. Lee
*Deputy Director of the United States Patent and Trademark Office*

CERTIFICATE OF CORRECTION (continued)
U.S. Pat. No. 8,710,079 B2

Page 2 of 2

In the Claims

Claim 6, column 38, lines 32-41, please change " 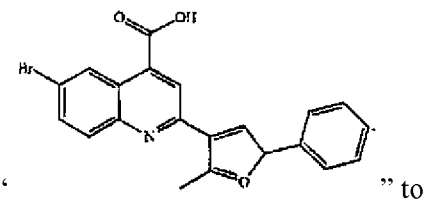 " to
-- 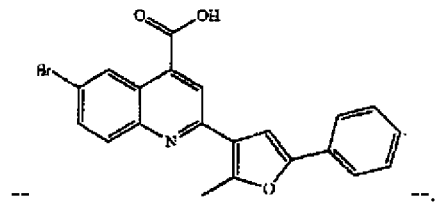 --.

Claim 6, column 38, lines 45-55, please remove " 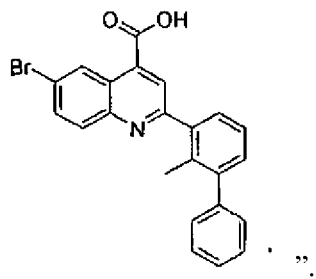 ".

Claim 6, column 39, lines 1-34, please remove
" 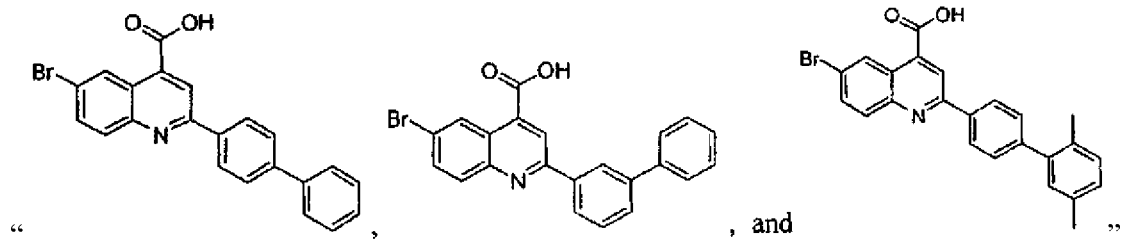 "

and add -- 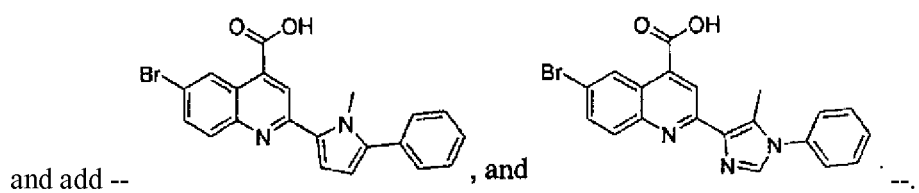 --.